(12) United States Patent
Vlodaver et al.

(10) Patent No.: US 8,834,410 B2
(45) Date of Patent: *Sep. 16, 2014

(54) MEDICATION DELIVERY DEVICE

(75) Inventors: Aner Vlodaver, Eden Prairie, MN (US); Benhoor Soumekh, Minnetonka, MN (US)

(73) Assignee: Alternamedics LLC, Eden Prairie, MN (US)

( * ) Notice: Subject to any disclaimer, the term of this patent is extended or adjusted under 35 U.S.C. 154(b) by 163 days.

This patent is subject to a terminal disclaimer.

(21) Appl. No.: 13/562,418

(22) Filed: Jul. 31, 2012

(65) Prior Publication Data

US 2012/0296268 A1 Nov. 22, 2012

Related U.S. Application Data

(63) Continuation of application No. 13/561,199, filed on Jul. 30, 2012, now Pat. No. 8,568,348, which is a continuation of application No. 13/180,076, filed on Jul. 11, 2011, which is a continuation-in-part of application No. 11/246,535, filed on Oct. 7, 2005, now abandoned.

(60) Provisional application No. 60/674,394, filed on Apr. 22, 2005.

(51) Int. Cl.
*A61M 3/00* (2006.01)
*A61M 1/00* (2006.01)
*A61M 5/00* (2006.01)
*A61M 31/00* (2006.01)

(52) U.S. Cl.
USPC ................ 604/43; 604/27; 604/257; 604/275

(58) Field of Classification Search
USPC ........... 604/27, 30, 35, 36, 37, 39, 43, 48, 73, 604/93.01, 94.01, 181, 183, 185, 187, 212, 604/213, 217, 257, 275, 276, 911, 182; 606/162
See application file for complete search history.

(56) References Cited

U.S. PATENT DOCUMENTS

| | | | | |
|---|---|---|---|---|
| 989,839 | A | * | 4/1911 | Fowler .......................... 604/276 |
| 1,450,612 | A | | 4/1923 | Schultz |
| 2,075,577 | A | | 9/1937 | Clement |
| 2,719,523 | A | | 10/1955 | Van Gierke |
| 2,737,953 | A | | 3/1956 | Wiltein |
| 2,879,768 | A | * | 3/1959 | Anderson ....................... 604/39 |
| 3,620,418 | A | | 11/1971 | Stevens et al. |
| 4,034,759 | A | | 7/1977 | Haerr |
| 4,201,212 | A | | 5/1980 | Bradley |

(Continued)

FOREIGN PATENT DOCUMENTS

| | | |
|---|---|---|
| EP | 0 234 061 | 9/1987 |
| EP | 0 243 261 | 10/1987 |

(Continued)

*Primary Examiner* — Kami A Bosworth
*Assistant Examiner* — Shefali Patel
(74) *Attorney, Agent, or Firm* — Fish & Richardson, P.C.

(57) ABSTRACT

An ear medication delivery device for delivering a treatment fluid and retaining the treatment fluid within an ear canal of a patient. The ear medication delivery device can retain the treatment fluid in contact with the ear canal or an eardrum of the patient for a desired time period to provide a therapeutic benefit. In some embodiments, an earplug device can be provided in several sizes for an optimal sealing fit in the ear canal.

28 Claims, 14 Drawing Sheets

(56) References Cited

U.S. PATENT DOCUMENTS

| | | | |
|---|---|---|---|
| 4,206,756 A | | 6/1980 | Grossan |
| 4,258,714 A | * | 3/1981 | Leopoldi et al. ............... 604/118 |
| 4,333,460 A | | 6/1982 | Miller |
| 4,573,977 A | | 3/1986 | Crawford |
| 5,058,606 A | * | 10/1991 | Malkoff ...................... 128/864 |
| 5,176,654 A | * | 1/1993 | Schreiber ...................... 604/181 |
| 5,273,531 A | * | 12/1993 | Knoepfler ...................... 604/58 |
| 5,364,343 A | | 11/1994 | Apolet et al. |
| 5,474,541 A | | 12/1995 | Ritsky et al. |
| 5,509,921 A | | 4/1996 | Karell |
| 5,662,605 A | | 9/1997 | Hurwitz |
| 5,674,196 A | * | 10/1997 | Donaldson et al. ........ 604/93.01 |
| 5,685,851 A | | 11/1997 | Murphy et al. |
| 5,715,850 A | | 2/1998 | Markgraaf |
| D403,766 S | | 1/1999 | Miller-Roach |
| 5,865,183 A | | 2/1999 | Hirschebain |
| 5,868,139 A | | 2/1999 | Zeece, Sr. |
| 5,944,711 A | | 8/1999 | Pender |
| 5,957,136 A | * | 9/1999 | Magidson et al. ............ 128/864 |
| 6,045,528 A | | 4/2000 | Arenberg et al. |
| 6,059,803 A | | 5/2000 | Spilman |
| 6,152,940 A | | 11/2000 | Carter |
| 6,155,987 A | | 12/2000 | Scherl |
| 6,210,358 B1 | | 4/2001 | Roger |
| 6,406,484 B1 | | 6/2002 | Lang |
| 6,458,094 B1 | * | 10/2002 | McMahon et al. ............... 604/35 |
| 6,485,451 B1 | | 11/2002 | Roberts et al. |
| 6,706,023 B1 | * | 3/2004 | Huttner et al. ................ 604/264 |
| 6,764,470 B2 | | 7/2004 | Dimick |
| 2003/0220585 A1 | | 11/2003 | Hissong |
| 2004/0097997 A1 | | 5/2004 | Di Cecco |
| 2004/0172005 A1 | | 9/2004 | Arenberg et al. |
| 2010/0198135 A1 | | 8/2010 | Morriss et al. |

FOREIGN PATENT DOCUMENTS

| | | |
|---|---|---|
| EP | 0 410 318 | 1/1991 |
| EP | 0 556432 | 8/1993 |
| EP | 0 744 168 | 11/1996 |
| EP | 1 407735 | 4/2004 |
| FR | 2551 657 | 9/1983 |
| FR | 2596645 | 4/1986 |
| FR | 2600883 | 7/1986 |
| FR | 2761 259 | 3/1997 |
| GB | 2 257 912 | 1/1993 |
| GB | 2318736 | 7/1998 |
| WO | WO 87/06456 | 11/1987 |
| WO | WO 93/05739 | 4/1993 |
| WO | WO 96/14098 | 5/1996 |
| WO | WO 97/42921 | 11/1997 |
| WO | WO 0107100 | 2/2001 |
| WO | WO 01/21118 | 3/2001 |
| WO | WO 02083203 | 10/2002 |
| WO | WO 03/103748 | 12/2003 |
| WO | WO 2004/030589 | 4/2004 |

* cited by examiner

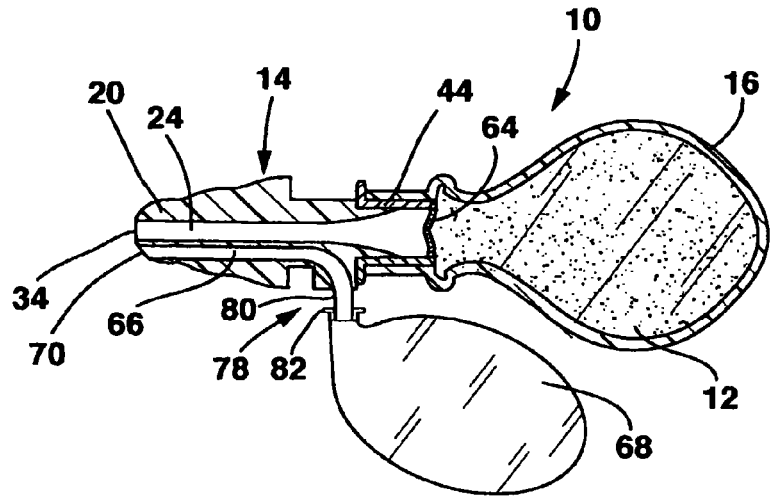
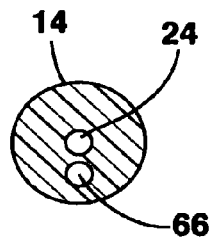
FIG. 11
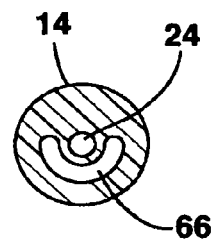
FIG. 12
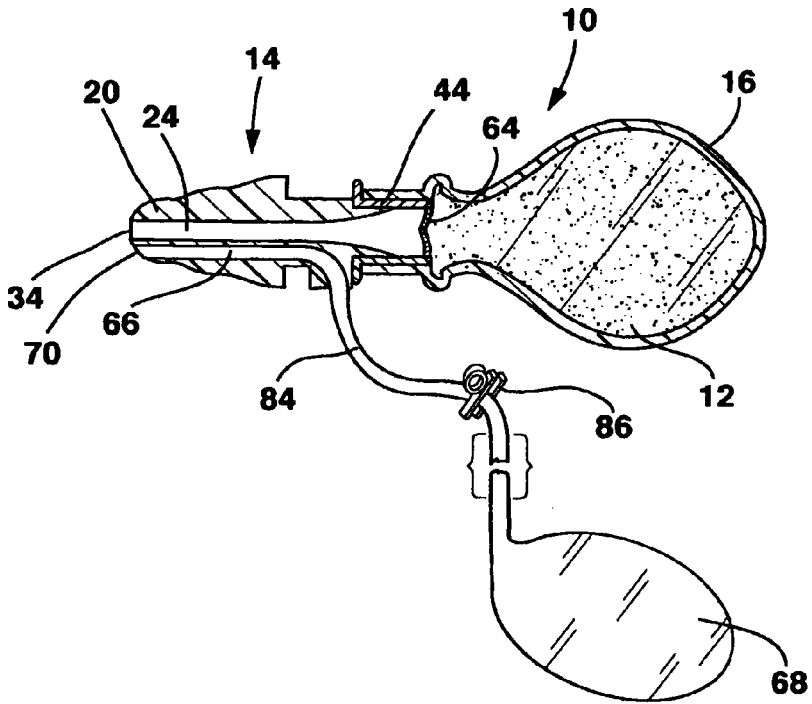

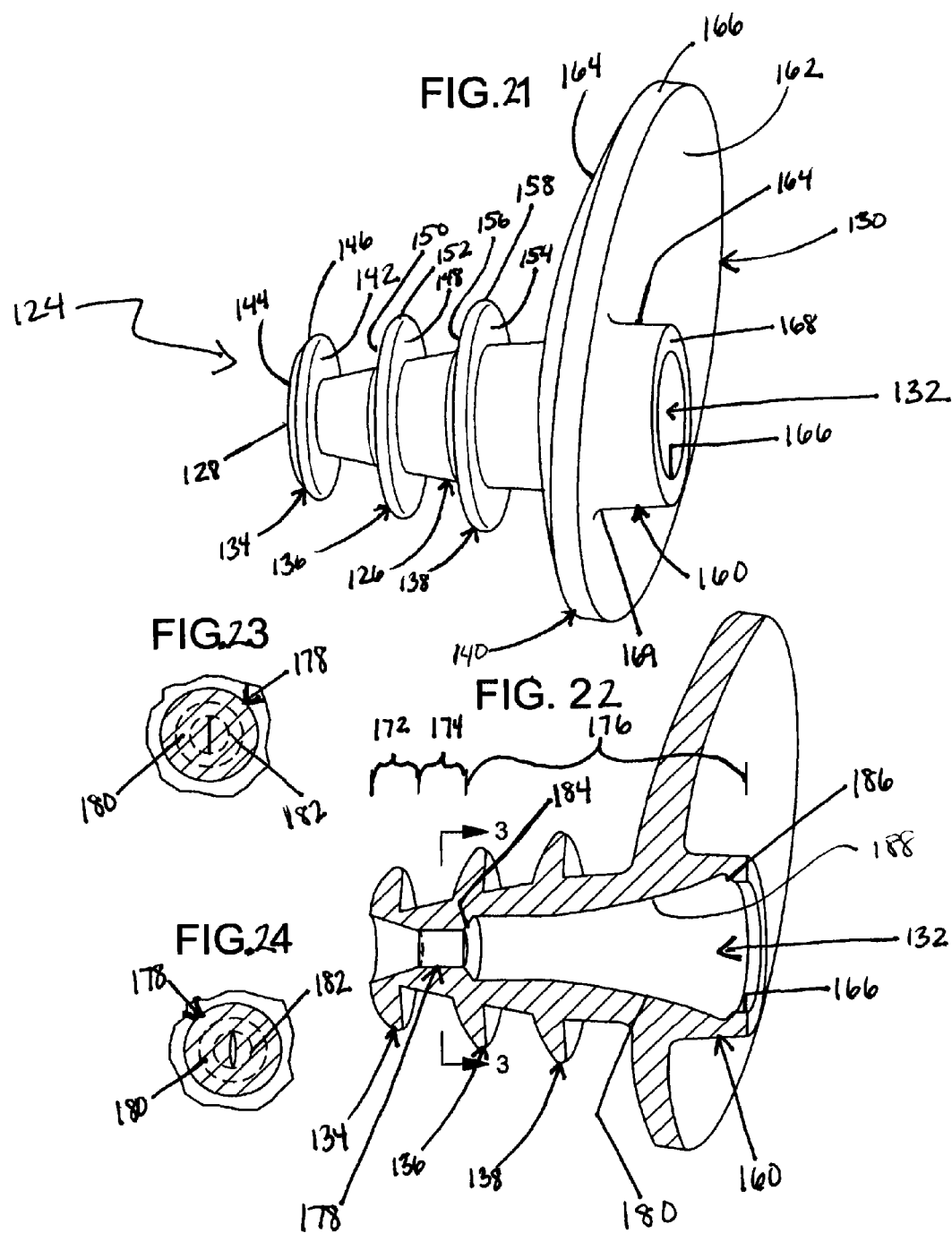

MEDICATION DELIVERY DEVICE

This application is a continuation of application Ser. No. 13/561,199 filed Jul. 30, 2012 entitled "Medication Delivery Device," which is a continuation of application Ser. No. 13/180,076 filed Jul. 11, 2011 entitled "Medication Delivery Device," which is a continuation-in-part of application Ser. No. 11/246,535 filed Oct. 7, 2005 entitled "Medication Delivery Device," which claims the benefit of U.S. Provisional Application No. 60/674,394 filed Apr. 22, 2005 entitled "Ear Washing and Medication Delivery Device."

FIELD OF THE INVENTION

The present invention is directed to devices and methods for treating maladies, particularly of the external ear canal, middle ear and eardrum and more particularly to such devices and methods that supply treatment fluids to the external ear canal and into the middle ear through the eardrum where a tympanostomy tube or a perforation is present.

BACKGROUND OF THE INVENTION

There are many medical conditions related to the middle ear and external ear canal that affect a large patient population. Among these conditions are otalgia (ear pain), otitis media (bacterial or viral infection of the middle ear), otitis externa (commonly known as swimmer's ear; an infection of the outer ear that causes inflammation), post tympanostomy tube otorrhea ("PTTO") (drainage from middle ear after tube placement), otorrhea with tympanic membrane perforation (drainage from middle ear drum rupture that can be a complication of a middle ear infection) and cerumen otic impaction (ear wax debris). Many of these conditions are common and, from a medical perspective, are prioritized roughly as listed.

The skin on the outer part of the external ear canal has special glands that produce cerumen, commonly called earwax (shown in the Figures labeled 6). Cerumen traps particles of dust and dirt and repels water thus helping to protect the delicate eardrum (shown in the Figures labeled 8) from damage. The earwax, and any trapped dust or dirt, is moved gradually out of the external ear canal by the lining of the ear canal. Eventually, the wax dries and falls out of the ear in small flakes.

Normal cerumen production is good and healthy for the ear. But, cerumen can be produced in excess where it can block the ear canal. Also, normal production amounts of cerumen can be pushed into the external ear canal especially while trying to remove the cerumen by cotton swabs, pencils, fingers and the like. Sometimes the attempt to remove cerumen pushes it further into the external ear canal where it contacts and is compressed against the eardrum 8. This condition, called cerumen impaction, can result in temporary hearing loss that gradually worsens, earache, ringing in the ear (tinnitus) or a feeling of being stuffed or full. The incidence of cerumen impactions varies as a function of age. In normal young adults the incidence is around 5%, while in the geriatric population (>65 years) the incidence is as high as 34%.

Otitis media is an acute or chronic inflammation of the middle ear that often manifests itself as earache, fever, hearing loss, and sometimes rupture of the tympanic membrane. 62% of children will experience at least one middle ear infection by age one and 83% will experience at least one middle ear infection by age three. There are about 30-35 million cases in the US per year of otitis media.

This condition alone accounts for 3% of all patient visits to hospitals and physicians and is the most common specifically treated childhood disease. The estimated cost of each episode of an ear infection is $90-$150 for an office visit and treatment and 1-2 days off for an adult parent care giver. In total, this translates into more than $1 billion annually in visits to the doctor in the US alone. The average total cost of treatment of ear infections for children is $1,093. In total, the cost of surgical insertion of tympanostomy tubes in the US to treat otitis media is over $2 billion annually. Further, otitis media is the #1 reason for an antibiotic prescription in the US.

Otitis Externa is an inflammation of the external auditory canal. In 1998, there were approximately 5,179,000 cases of otitis externa diagnosed in the United States. In the US, otitis externa occurs in 4 out of every 1000 Americans every year.

Approximately 2 million tympanostomy tubes are placed in children in the United States each year. One common complication following the placement of tympanostomy tubes is the development of purulent ear drainage which often causes discomfort after tube placement. This condition is called post tympanostomy tube otorrhea ("PTTO"). Approximately 10 to 20% of children will experience PTTO during the period immediately following the procedure to place the tube. The incidence of delayed PTTO is approximately 30% while the tube is still in place. The incidence of PTTO is even higher among infants and among young children who have recurrent infections.

As can be seen, there are a large number of medical conditions affecting the external ear canal, middle ear and eardrum and a large number of patients affected by these medical conditions. Consequently, there have been developed therapies and therapeutic devices to treat these conditions especially by the application of medicaments to the affected areas. For example, a common dropper is often used to deliver a solution for irrigation of the external ear canal or to deliver therapeutic solutions to the external ear canal 26 or eardrum 8. One problem with such droppers is that the dropper must be loaded with the desired fluid prior to using the dropper. This is usually accomplished by depressing a flexible bulb on the end of the dropper and inserting the opposite end of the dropper in the desired solution. The flexible bulb is released creating a vacuum that draws the fluid into the dropper. Thereafter, care must be taken to prevent the inadvertent discharge of the fluid. This process is cumbersome and messy and often results in spillage and dripping of the fluid.

Once the dropper has been loaded with fluid, the user inserts the end of the dropper in the patient's ear and squeezes the bulb to discharge and deliver the fluid to the patient's ear canal. If the user squeezes the bulb too hard, a pressurized stream of fluid exits the dropper and contacts the patient's ear, particularly the patient's eardrum 8, which can cause pain or discomfort.

The dropper is then removed from the patient's ear. Gravity holds the fluid in the patient's ear. Consequently, the patient must be on his or her side when the fluid is delivered so that the fluid will enter and be retained in their ear. Thereafter, if it is desired that the fluid continue to be retained in the patient's ear for therapeutic purposes, the patient must continue to be on his or her side or else the fluid will drain from their ear. Requiring the patient to be on their side for delivery of the fluid and to retain the fluid in the external ear canal is problematic especially for small, restless or ambulatory children or adults.

Further, once it is desired to remove the fluid from the ear, the patient turns their head so that gravity can cause the fluid to drain from the ear canal. The fluid is then recovered and the patient cleaned up from the fluid, particularly from the drainage path of the fluid, by the application of towels or cotton balls. This is also a messy process that spreads the used fluid over portions of the patient or the patient's clothes and surroundings. All these problems with droppers are in need of solutions.

Several devices have been developed to address some of these problems. For instance, U.S. Pat. No. 4,528,714 issued to Norbert Leopoldi and William P. Heinrich on Mar. 31, 1981 entitled "Ear Syringe" discloses an ear syringe having a bulb for containing fluid and a stem for entering the external ear canal to inject the fluid from the bulb into the external ear canal to flush out and remove foreign matter or cerumen. The '714 device has a built-in pressure regulator valve to control the discharge velocity of the fluid exiting from the stem of the device. This minimizes the chance that a pressurized stream of fluid will contact the eardrum 8 and build up fluid pressure in the external ear canal and subsequently on the eardrum 8 to cause discomfort or pain to the patient while using the device. This device does not address the problems of the mess associated with filling the device or administering and removing the fluid to and from the ear canal. Further, this device does not address the problem requiring the patient to be on his or her side for the delivery of fluid or having to retain this position to keep the fluid in the ear canal.

Another device to treat maladies of the external ear canal, middle ear and ear drum is disclosed in U.S. Pat. No. 5,674, 196 issued to John Donaldson and Krista Donaldson on Oct. 7, 1997 entitled "Device for Introducing Medical Fluid into the Human Ear." This patent discloses a device for administering medical fluid to the eardrum 8 or external ear canal 26. The '196 device includes an earplug that is inserted into the ear canal. The earplug fits snugly in the external ear canal and substantially seals the ear canal. The earplug has a conduit passing through it to allow fluid from a syringe to be introduced to the external ear canal between the earplug and the eardrum 8. Once the medical fluid is introduced into the ear, the conduit can be sealed to retain the medical fluid in the ear canal. In this way, the medical fluid comes into and remains in contact with the external ear canal 26 or eardrum 8 or both so that the medical fluid can perform its intended therapeutic function.

But, this device does not address the problems associated with putting fluid into the syringe. Further, this device does not address the problem of eliminating the mess associated with removing the fluid from the patient's ear canal.

So, there exists a need for a device to deliver therapeutic fluids to the external ear canal 26 or eardrum 8 has some or all of the following characteristics: is easy to fill or pre-filled with treatment fluid (to eliminate the associated mess); allows the fluid to be delivered in either a supine or upright position; allows the patient to be ambulatory after applying the fluid; seals the fluid in the ear canal; allows the fluid delivery bulb to be separated from the device in contact with the patient's ear; and allows the used treatment fluid to be easily and cleanly removed from the patient's ear at the appropriate time.

SUMMARY OF THE INVENTION

The present invention is a device and method for treating maladies, particularly of the external ear canal, middle ear and eardrum. The device in a preferred embodiment comprises an earplug and a delivery bulb, reservoir, syringe or ear dropper that holds treatment fluid (collectively "treatment fluid reservoir"). A lumen extends through the earplug and connects the treatment fluid reservoir to an orifice located at the distal end of the earplug. A one-way valve is located along the lumen to allow treatment fluid to only flow from the treatment fluid reservoir to the orifice and not vice versa. The earplug forms a seal with the patient's external ear canal and, combined with the one-way valve, retains treatment fluid in the patient's external ear canal where it can perform its therapeutic function. In one embodiment, the invention includes a collection bag connected through the earplug to an orifice near the distal end of the earplug to collected waste treatment fluid.

A therapeutic method comprises using a device, as disclosed herein, to deliver treatment fluids to the patient's external ear canal for irrigation, for the therapeutic benefit of the treatment fluids for the short term, for longer term therapeutic benefit by delivering and retaining the treatment fluid in contact with the patient's external ear canal or eardrum for a desired time period to provide a therapeutic benefit or to deliver treatment fluid to a patient's external ear canal where it can pass into the patient's middle ear through a tympanostomy tube placed in the patient's eardrum or ear through an eardrum perforation.

In a further embodiment, a treatment fluid delivery device is disclosed for treating maladies of a patient's body orifice or body cavity that is substantially as described in connection with the device for treating maladies of the external ear canal, middle ear and eardrum. In this embodiment, the earplug is modified in size, shape and possibly other physical properties such as flexibility, rigidity and pliancy to become a plug that accommodates forming a sealing fit with the orifice or body cavity to which it is applied. The invention includes a corresponding method for treating maladies of a patient's body orifice or body cavity that comprises using a device, as disclosed herein, to deliver treatment fluids to the patient's body orifice or body cavity and retaining the treatment fluid in contact with the patient's body orifice or body cavity for a desired time period to provide a therapeutic benefit or to deliver treatment fluid to a patient's body orifice or body cavity.

It is therefore an object of the invention in one embodiment to provide a device that delivers treatment fluids to the patient's external ear canal for irrigation.

It is therefore an object of the invention in one embodiment to provide a device that delivers treatment fluids to the patient's external ear canal for the therapeutic benefit of the treatment fluids for the short term.

It is therefore an object of the invention in one embodiment to provide a device that delivers treatment fluids to the patient's external ear canal for longer term therapeutic benefit by delivering and retaining the treatment fluid in contact with the patient's external ear canal or eardrum for a desired time period to provide a therapeutic benefit.

It is therefore an object of the invention in one embodiment to provide a device that delivers treatment fluids to the patient's external ear canal to deliver treatment fluid to a patient's external ear canal where it can pass into the patient's middle ear through a tympanostomy tube placed in the patient's eardrum or through an eardrum perforation.

It is also an object of the invention in one embodiment to make an ear syringe that requires less effort than previous devices to direct solution into the ear because the mechanism for holding treatment fluids is already filled with treatment fluid and is connected to the earplug.

It is also an object of the invention in one embodiment to make an ear syringe that is easier to use than previous devices since fewer steps are needed to deliver the treatment fluids into the ear.

It is also an object of the invention in one embodiment to make an ear syringe that produces less mess in introducing solution into the ear than currently available devices since the mechanism for holding treatment fluid is already filled with treatment fluid and is connected to the earplug.

It is also an object of the invention in one embodiment to make an ear syringe that does not allow the treatment fluid to be absorbed by the device as compared to a cotton ball.

It is also an object of the invention in one embodiment to make an ear syringe that may be applied to a patient who may be standing, sitting or in a prone position as compared to prior art devices where the patient needs to remain laying down, particularly on his or her side, after delivery of treatment fluids.

It is also an object of the invention in one embodiment to make an ear syringe that, following the administration of the treatment fluid, allows the patient to move around and be ambulatory and does not have to remain motionless and on their side as compared with prior art devices.

It is therefore an object of the invention in one embodiment to provide a device that delivers treatment fluids to the patient's body orifice or body cavity.

It is therefore an object of the invention in one embodiment to provide a device that delivers treatment fluids to the patient's body orifice or body cavity for the therapeutic benefit of the treatment fluids for the short term.

It is therefore an object of the invention in one embodiment to provide a device that delivers treatment fluids to the patient's body orifice or body cavity for longer term therapeutic benefit by delivering and retaining the treatment fluid in contact with the patient's body orifice or body cavity for a desired time period to provide a therapeutic benefit.

It is therefore an object of the invention in one embodiment to provide a device that delivers treatment fluids to the patient's body orifice or body cavity that requires less effort or is easier to use than previously known devices.

It is also an object of the invention in one embodiment to provide a device that delivers treatment fluids to the patient's body orifice or body cavity that may be applied to a patient who may be standing, sitting or in a prone position as compared to prior art devices where the patient needs to remain laying down, particularly on his or her side, after delivery of treatment fluids.

It is also an object of the invention in one embodiment to provide a device that delivers treatment fluids to the patient's body orifice or body cavity that, following the administration of the treatment fluid, allows the patient to move around and be ambulatory and does not have to remain motionless.

These and other objects of the invention will be clear from the description contained herein and particularly with reference to the following Detailed Description of the Invention and the associated Drawings.

In a further embodiment, a treatment fluid delivery device is disclosed for treating maladies of the external ear canal, middle ear and eardrum. In this embodiment, the earplug is formed of a soft, resilient, molded material, a portion of which engages the ear canal. The internal ear engaging portion presents three minor disks of progressively different sizes on an external surface thereof. An internal lumen extends through the length of the treatment fluid delivery device. The external portion includes a major disk and an annular medication applicator receiving portion in fluid communication with the internal lumen. The internal lumen extends through the internal ear engaging portion and the external portion.

The internal lumen of the treatment fluid delivery device is contoured, shaped and dimensioned to receive a portion of a medication applicator such as an ear dropper, an eye dropper, a syringe, or similar device. The internal lumen of the treatment fluid delivery device and the medication applicator are dimensioned such that a liquid tight seal is formed between the two. A molded, resilient valve is contained in the ear engaging portion and controls fluid flow through a segment of the internal lumen and is integrally formed of the same material as the treatment fluid delivery device by, for example, injection molding. The valve opens in either direction under a preselected fluid pressure and closes below the preselected fluid pressure.

BRIEF DESCRIPTION OF THE DRAWINGS

FIG. 10 is a side cross-sectional view of an alternate embodiment of the present invention with a waste collection bag.

FIG. 11 is a cross-sectional view of the earplug of the embodiments of FIGS. 10 and 13 showing the placement of the lumen and collection tube.

FIG. 12 is a cross-sectional view of an alternate embodiment of the earplug of the embodiments of FIGS. 10 and 13 showing an alternate placement of the lumen and collection tube.

FIG. 13 is a side cross-sectional view of an alternate embodiment of the invention of FIG. 10.

FIG. 21 is a perspective view of the treatment fluid delivery device according to an example embodiment of the invention.

FIG. 22 is a cross-sectional view of the embodiment of FIG. 21.

FIG. 23 is a sectional view of the closed valve of the embodiment of FIG. 21.

FIG. 24 is a sectional view of the open valve of the embodiment of FIG. 21.

DETAILED DESCRIPTION

Figure 1:
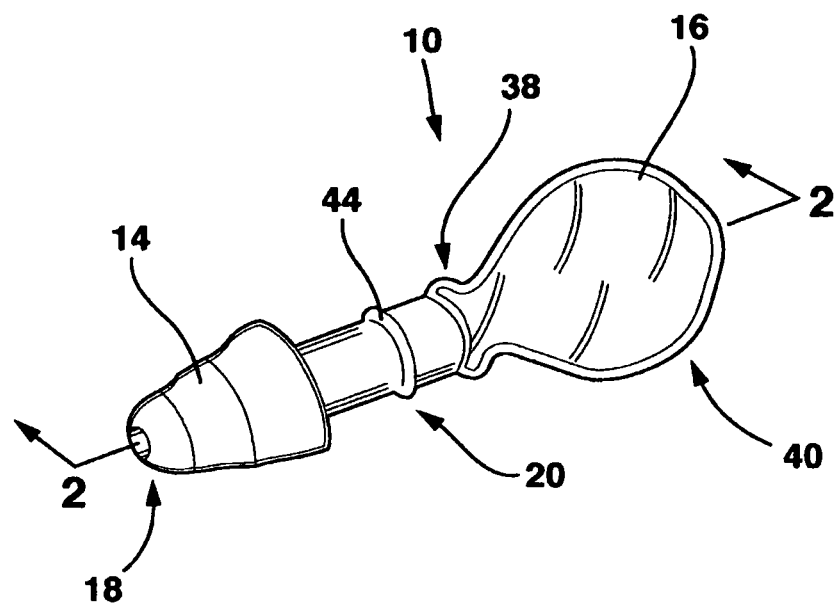
FIG. 1 is a perspective view of an embodiment of the present invention.

Throughout the description, like members, elements or parts, wherever referenced or described are referred to by like reference numbers. Unless otherwise described, the description and functioning of an element set out in one portion of the application applies to the element referred to by the same reference number in another portion of the description. Further, the present description includes description of several embodiments of the invention. Again, reference to or description of an element in connection with one embodiment refers to the physical attributes, characteristics or function of an element wherever set forth in the description.

The present invention is an ear medication delivery device, shown in the Figures generally labeled 10, and an associated therapeutic method of treating ailments of the external ear canal, middle ear and eardrum 8. The purpose of the device is to provide medicament such as antibiotics, antifungals, steroids and analgesics such as are commonly used for swimmers ear and other ear infections and cleansing fluid or irrigation fluid, collectively treatment fluid 12, to a patient's external ear canal 26, eardrum 8, middle ear or all of the above and in one embodiment, retain the treatment fluid 12 in the patient's external ear canal 26 in contact with the ear canal, middle ear and/or eardrum 8.

The device 10 is comprised of an earplug 14 and a delivery bulb 16. Earplug 14 has a distal end 18, a proximal end 20, an outer body 22 and a lumen 24. The function of outer body 22 is to contact and provide a seal with the patient's external ear canal 26. Consequently, outer body 22 is preferably relatively frustoconical in shape, made of a somewhat pliable hypoallergenic material that is non-reactive with the tissue of the external ear canal like compressible resilient elastomeric foam, rubber, silicone, silicone putties, vinyl or acrylics and dimensioned so that the distal end 18 of the earplug 14 may be placed into the external ear canal 26 but that the portions of the outer body 22 nearer the proximal end 20 of the earplug 14 will come into sealing contact with the patient's external ear canal 26. Because body 22 is somewhat pliable, it will conform to the shape of the patient's external ear canal 26 as the earplug 14 is placed in the patient's external ear canal 26 as will be explained hereafter. Since ear canals become larger with age, it may be desirable to produce the device 10 with several sizes for the outer body 22 in order to have an optimal sealing fit in the patient's external ear canal 26.

Although outer body 22 has been described as being preferably relatively frustoconical in shape, outer body 22 can take on any shape so long as outer body 22 is able to perform the function of contacting and providing a seal with the patient's external ear canal 26. Without limiting the possible shapes for outer body 22, outer body 22 could also be relatively cylindrical, conical, prismatic, prolate spheroidal or pyramidal. Further, outer body 22, in whatever form it takes, could have smooth sides, ridges or undulations. Further, outer body 22 in whatever form it takes could have variable flexibility, rigidity and pliancy depending on the treating or recommending physician's preference considering the patient's age and anatomy, the disease or malady, the progression or state of the disease or malady or other conditions or factors that, based on the physician's judgment, would affect such a choice of material and properties.

Figure 2:
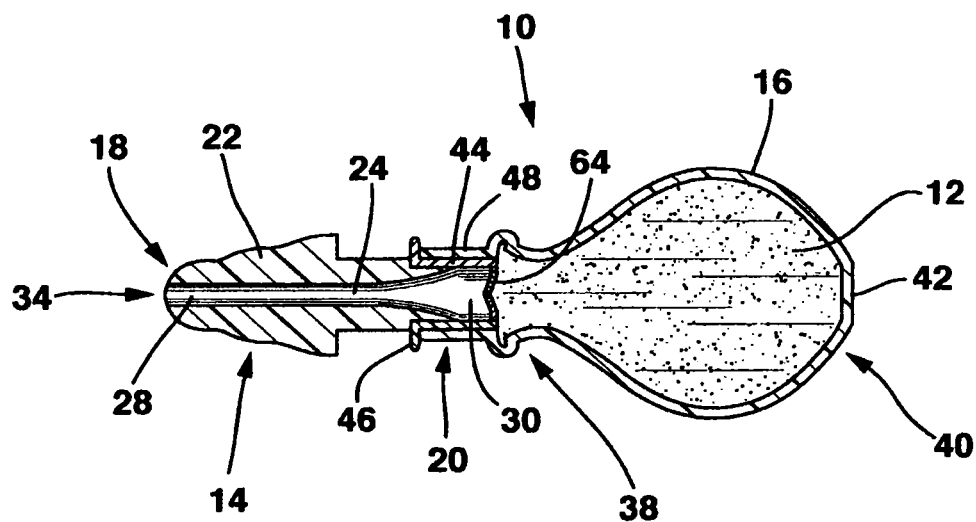
FIG. 2 is a side cross-sectional view of the embodiment of FIG. 1.

As stated above, earplug 14 has a lumen 24. Lumen 24 runs essentially entirely through earplug 14 and has a distal end 28 and a proximal end 30. In the embodiment of FIGS. 1 and 2, lumen 24 is formed by removing the material of outer body 22 or by molding the earplug 14 so that a lumen 24 is formed. In another embodiment, shown in FIG. 3, lumen 24 is formed in a separate tube 32 that is placed within earplug 14 where the tube 32 has a hollow lumen 24 extending along the entire length of tube 32. Tube 32 may be made of the same or different material than earplug 14.

The length of lumen 24, whether alone or in the embodiment with tube 32, will vary with the size of the earplug 14. But, it is preferred, but not necessary, that the earplug 14 be relatively short, and consequently that the lumen 24 will be relatively short, so that the entire device 10 is compact and easy to be held in a user's hand (FIGS. 1-4).

Figure 4:
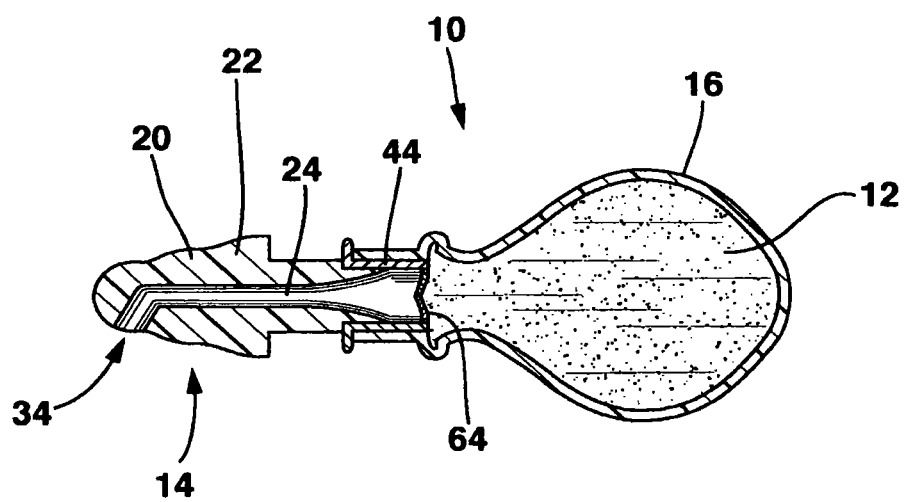
FIG. 4 is a side cross-sectional view of an alternate embodiment of FIG. 1.

Lumen 24 extends from the delivery bulb 16 to the distal end 18 of the earplug 14 where the lumen 24 terminates in an orifice 34. Lumen 24 acts as the channel for treatment fluid 12 to move from the delivery bulb 16 to and out of the orifice 34. In the preferred embodiment of the invention, orifice 34 is located at the ultimate distal end 18 of earplug 14. But, as shown in FIG. 4, orifice 34 may be located along the surface of the outer body 22 away from the ultimate distal end 18 of earplug 14 but still before the part of outer body 22 that contacts and provides a seal with the patient's external ear canal 26. This offset configuration will result in the treatment fluid 12 leaving the orifice 34 and contacting the wall of the external ear canal near the orifice instead of leaving the orifice 34 with the possibility of directly contacting the user's eardrum 8. This offset configuration for the location of the orifice 34 may be particularly desirable where the user's eardrum 8 is inflamed or otherwise sensitive to contact by a pressurized stream of treatment fluid 12. In a further variant, several orifices 34 may be formed including combinations of an orifice 34 located at the ultimate distal end 18 of the earplug 14 and one or more orifices 34 located at offset locations located along the surface of the outer body 22 away from the ultimate distal end 18 of earplug 14 as described above or several orifices 34 located along the surface of the outer body 22 away from the ultimate distal end 18 of earplug 14 as described above but without an orifice 34 located at the ultimate distal end 18 of the earplug 14.

Figure 3:
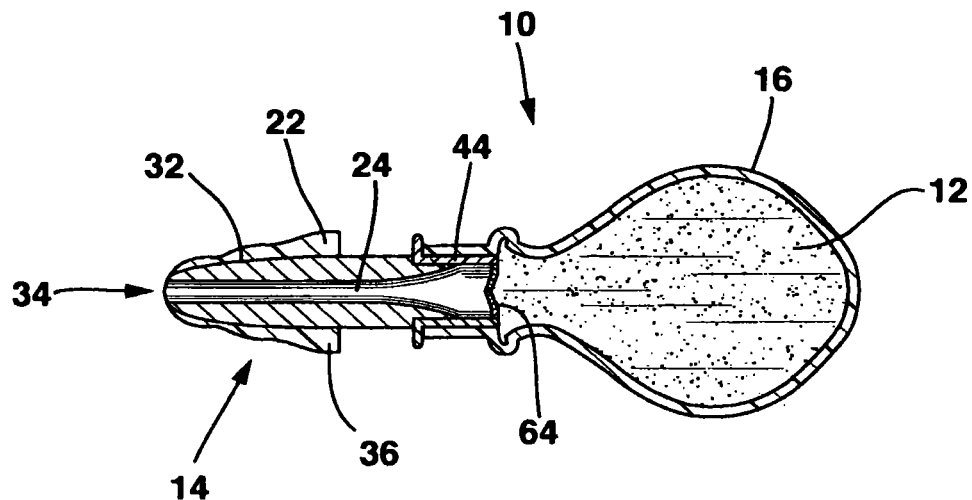
FIG. 3 is a side cross-sectional view and an alternate embodiment of the present invention.

Earplug 14, in the embodiment shown in FIG. 2, is made in one piece of somewhat pliable hypoallergenic material that is non-reactive with the tissue of the external ear canal like compressible resilient elastomeric foam, rubber, silicone, silicone putties, vinyl or acrylics by techniques such as molding and machining. However, as mentioned, earplug 14 may also be made of separate pieces combined together to make the earplug 14. For example, as shown in FIG. 3, the tube 32 and outer body 22 of earplug 14 are made separately, either of the same or different materials. The outer body 22 is then attached, by means well understood in the art, including but not limited to gluing, frictional fit, mechanical connection or threaded connection, to the outer surface 36 of the tube 32 so that the distal end 28 of the tube 32 is aligned with the orifice 34 of the earplug 14.

As mentioned, in this embodiment tube 32 and outer body 22 could be made of different material. For example, tube 32 could be made of a relatively rigid material such as is common for cannulae used for medical uses to provide a solid base for the device 10. Examples of such material includes, but is not limited to, silicone, polyvinylchloride (PVC), polyurethane, polyether urethane, polyether urethane urea, polyamide, polyacetal, polyester, poly ethylene-chlorotrifluoroethylene, poly tetrafluoroethylene (PTFE or "Teflon®"), styrene butadiene rubber, polyethylene, polypropylene, polyphenylene oxide-polystyrene, poly-a-chloro-p-xylene, polymethylpentene, polysulfone and other related biostable polymers. In this embodiment as well, outer body 22 is made of a somewhat pliable hypoallergenic material that is non-reactive with the tissue of the external ear canal like compressible resilient elastomeric foam, rubber, silicone, silicone putties, vinyl or acrylics by techniques such as molding and machining to allow it to be deformed into a sealing fit in the patient's external ear canal 26.

Figure 5:
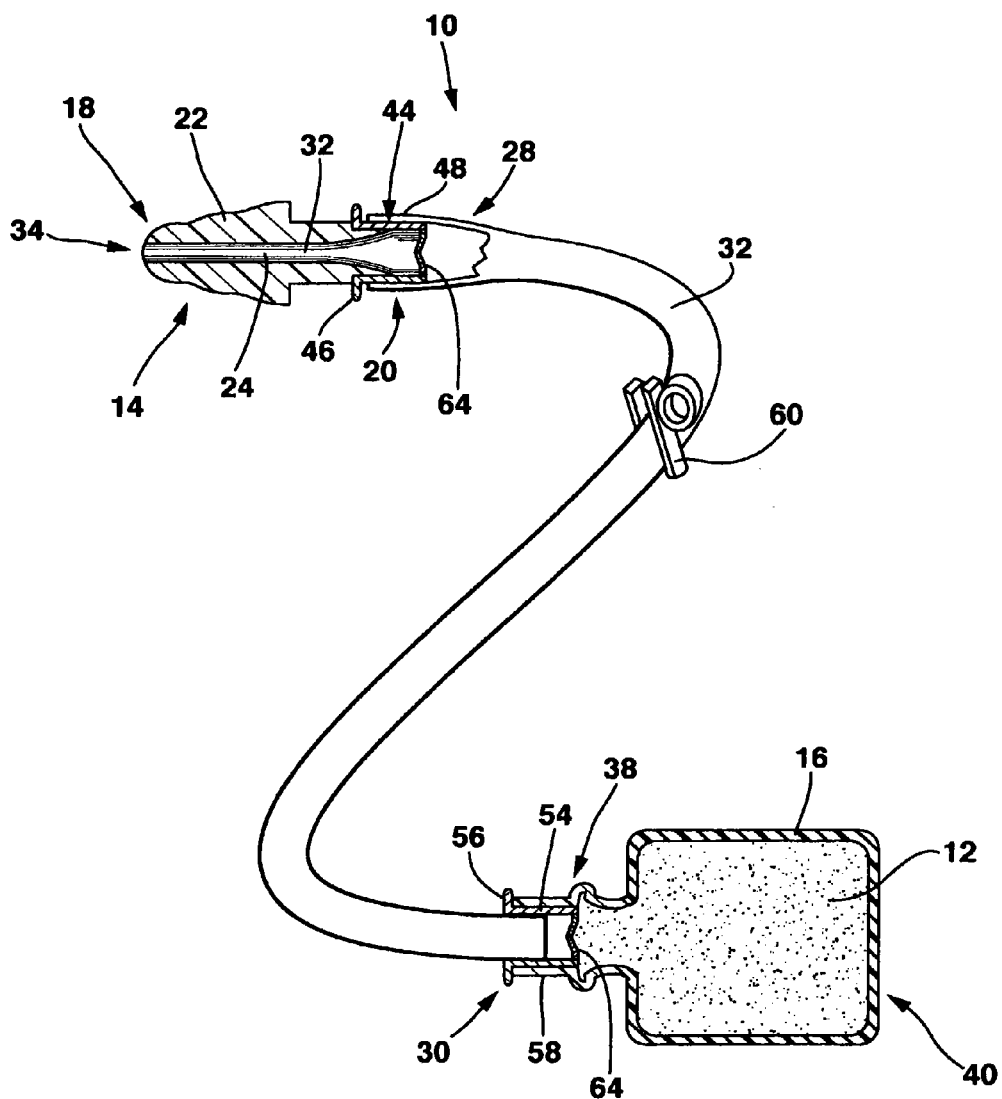
FIG. 5 is a side cross-sectional view of an alternate embodiment of the present invention.

In an embodiment shown in FIG. 5, earplug 14 is of a size to fit in the patient's external ear canal 26. But, tube 32 is quite long and flexible and extends beyond earplug 14 to essentially act as a conduit connecting the delivery bulb 16, which may be located a distance away from the earplug 14, to the earplug 14. Tube 32 in this embodiment may also include a pinch valve 60 located along tube 32 preferably near the distal end 28 of tube 32. The function of pinch valve 60 is to open or close the tube 32 to the passage of treatment fluid 12. Consequently, pinch valve 60 may take any of a number of forms well-known in the art. Pinch valve 60 is opened when it is desired for treatment fluid 12 to pass from the delivery bulb 16 to the earplug 14 but may be closed when tube 32 is separated from the earplug 14, as described hereafter, to prevent spillage of treatment fluid 12 from the tube 32.

As mentioned above, the device 10 includes a delivery bulb 16. The function of delivery bulb 16 is to store treatment fluid 12 and deliver the treatment fluid 12 to the earplug 14 at the appropriate time. In the preferred embodiment, delivery bulb 16 is generally typical of syringe bulbs used to irrigate the external ear canal and has a distal end 38 and a proximal end 40. Consequently, the delivery bulb 16 is preferably made of a flexible material such as vinyl or a rubber compound that allows the delivery bulb 16 to expand when fluid is placed into or drawn into the delivery bulb 16 and allows the delivery bulb 16 to be squeezed or compresses to expel the treatment fluid 12 from the delivery bulb 16 to and out of the earplug 14. Preferably, the material and thickness of delivery bulb 16 is such that when delivery bulb 16 is squeezed and then released, delivery bulb 16 on its own will return to its un-squeezed or un-compressed condition.

In a variant of this embodiment, delivery bulb 16 is made of a material or of a thickness of material that allows the delivery bulb 16 to expand when fluid is placed into or drawn into the delivery bulb 16 and allows the delivery bulb 16 to be squeezed or compresses to expel the treatment fluid 12 from the delivery bulb 16 to and out of the earplug 14 but that does not allow the delivery bulb 16, when squeezed and then released, to return to its un-squeezed or un-compressed condition. In this variant, the material of delivery bulb 16 could include, but not be limited to flexible rubber, soft thermoplastic material such as vinyl or a silicon elastomer or the thickness of the material of delivery bulb 16 could be reduced to make the delivery bulb 16 more pliant.

The delivery bulb 16 is preferably generally spherical and may, but is not required to have a flat spot or concavity 42 on the proximal end 40 of the delivery bulb 16 that provides an area for standing the delivery bulb 16 upright when it is disconnected from the earplug 14 as will be described hereafter. Although the preferred shape of the delivery bulb 16 is roughly spherical it is not required to be spherical. Other shapes may be used, including the lack of any predefined shape, so long as the delivery bulb 16 performs the functions described above. One of an almost limitless number of examples for shapes of the delivery bulb 16 is shown in FIG. 5 in connection with an alternate embodiment of the device 10. As shown in this example, the delivery bulb 16 has the shape of an elongated bladder. In a further variant of the delivery bulb 16, delivery bulb 16 could be a bellows that allows the delivery bulb 16 to expand as treatment fluid 12 is drawn in to the delivery bulb 16 and collapse as the treatment fluid 12 is expelled from the delivery bulb 16.

Figure 6:
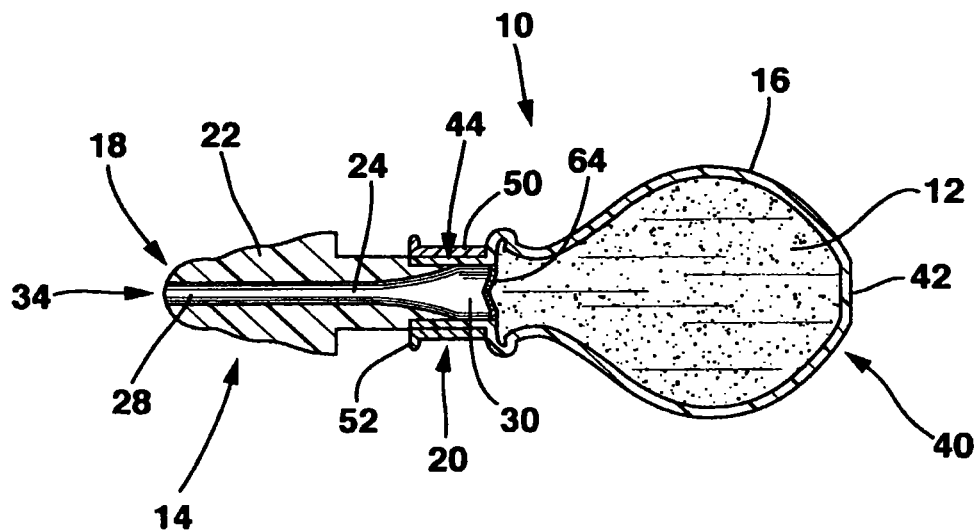
FIG. 6 is a side cross-sectional view of an alternate embodiment of the attachment mechanism of the present invention.
Figure 7:
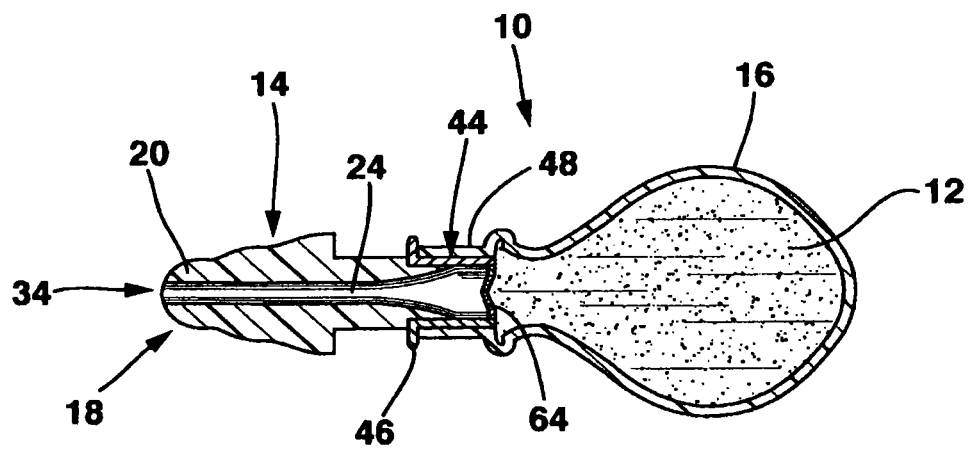
FIG. 7 is a side cross-sectional view of an alternate embodiment of the attachment mechanism of the present invention

Earplug 14 also preferably includes an attachment mechanism 44 located at the proximal end 20 of earplug 14. The function of attachment mechanism 44 is to sealingly connect the delivery bulb 16 to the earplug 14. In the case of one set of embodiments, the attachment mechanism 44 connects the earplug 14 to the proximal end 30 of tube 32. In one embodiment, as shown in FIG. 2, attachment mechanism 44 is a channel 46 formed at the proximal end 34 of earplug 14. Delivery bulb 16 has a sleeve 48 made of the extension of the material of delivery bulb 46 that fits into and around channel 46 to sealingly connect delivery bulb 16 to earplug 14 so that channel 46 and sleeve 48 interact in a male-female relationship, respectively. In a variant of this embodiment, shown in FIG. 6, delivery bulb 16 has a channel 50 formed at its distal end 38 and earplug 14 has a sleeve 52, made of the extension of the material of the earplug 12, that interact in a female-male relationship, respectively.

In the embodiment of FIG. 5, the delivery bulb 16 is located a distance away from the earplug 14. Tube 32 connects the delivery bulb 16 to the earplug 14 and forms the lumen 24 that allows treatment fluid 12 in the delivery bulb 16 to pass to and out of the earplug 14 through the orifice 34. As a result, in this embodiment, tube 32 extend from the distal end 18 of the earplug 14 to and out of the proximal end 20 of earplug 14 to the delivery bulb 16 where tube 32 is fluidly connected to allow treatment fluid 12 to flow from the delivery bulb 16 through the lumen 24 of the tube 32 to exit the tube 32 at the orifice 34. In this embodiment, because the tube 32 extends from the distal end 18 of the earplug 14 to and out of the proximal end 20 of the earplug 14, there is no need for an attachment mechanism 44 at the proximal end 20 of the earplug 14.

However, there is a need connect the proximal end 30 of the tube 32 to the delivery bulb 16. In this embodiment, the device 10 includes a delivery bulb attachment mechanism 54 that connects the proximal end 30 of the tube 32 to the delivery bulb 16. In the form shown in FIG. 5, delivery bulb attachment mechanism 54 is a channel 56 formed at the proximal end 30 of tube 32 and a sleeve 58 formed in the distal end 38 of delivery bulb 16 so that channel 56 and sleeve 58 interact in a male-female relationship, respectively. Alternately, delivery bulb attachment mechanism 54 could be a channel formed at the distal end 38 of delivery bulb 16 and a sleeve formed in the proximal end 40 of tube 32 so that the channel and sleeve interact in a female-male relationship, respectively.

Further, tube 32 could be integrally formed with the distal end 38 of delivery bulb 16 so that there is no need to have a delivery bulb attachment mechanism 54. In this variant, the tube 32 extends from the delivery bulb 16 to the earplug 14 where the distal end 28 of tube 32 may be connected to the proximal end 20 of the earplug 14 through the attachment mechanism 44 described above. This embodiment as well may include a connection between the tube 32 extending from the delivery bulb 16 to the proximal end 20 of the earplug 14 to the tube 32 located within the earplug 14 (in the embodiments having such a tube 32 in the earplug 14) or may be connected directly to the lumen 24 at the proximal end 20 of the earplug 14 (in those embodiments where lumen 24 is formed directly in the earplug 14).

Specific examples have been given for the structure of attachment mechanism 44 and delivery bulb attachment mechanism 54. However, the specific structure of these connections is not critical to the invention. It is clear that it is well understood in the art how to connect tubing together or to connect tubing to bags or implements. Consequently, it is intended that any well understood mechanism that performs the function of either attachment mechanism 44 or delivery bulb attachment mechanism 54 is within the scope of the invention.

Earplug 14 also includes a one-way valve 64. The function of the one-way valve 64 is to prevent the treatment fluid 12 from re-entering the delivery bulb 16 once the treatment fluid 12 has left the delivery bulb 16. In particular, this allows the treatment fluid 12 to remain in the external ear canal 26 for a desired period of time without exiting the device 10 through the proximal end 20 of the lumen 24. Further, this allows the delivery bulb 16 to be removed from the earplug 14 when the earplug 14 is in position in a patient's external ear canal 26. This allows the earplug 14 to retain the treatment fluid 12 in the patient's external ear canal 26 while minimizing the inconvenience of having the delivery bulb 16, with its accompanying bulk, attached to the earplug 14 while the treatment fluid 12 is retained in the patient's external ear canal performing its therapeutic purposes.

The one-way valve 64 is preferably, but not limited to being, located close to the delivery bulb 16 so that when delivery bulb 16 is separated from the earplug 14 after the treatment fluid 12 has been expelled from the delivery bulb 16, virtually no treatment fluid 12 remains proximal to the one-way valve 64 to spill when the delivery bulb 16 is removed. Although the one-way valve 64 is preferably located-close to the delivery bulb 16, it is not required to be so placed. The one-way valve 64 may be located anywhere along the lumen 24 in whatever form lumen 24 takes. Further, more than one one-way valve 64 may be located along the lumen 24.

As stated, the function of one-way valve 64 is to prevent the treatment fluid 12 from re-entering the delivery bulb 16 once the treatment fluid 12 has left the delivery bulb 16. The present invention intends that any valve that performs this function may be used as the one-way valve 64. However, without excluding any possible valves that meet this functional criteria, the following valve types may be used as the one-way valve 64: slit valves, check valves including swing valves (monocuspid, bicuspid, tricuspid), lift valves, ball valves, tilting disk valves, dual plate (leaflet) valves, diaphragm valves, flap valves and general valves including ball valves, butterfly valves, check valves, diaphragm valves, gate valves, globe valves, plug valves, duck bill valves and pinch valves. In this way, one-way valve 64 allows treatment fluid 12 contained within the delivery bulb 16 to be dispensed by squeezing the delivery bulb 16, sending the treatment fluid 12 past the one-way valve 64, through the lumen 24 contained within the earplug 14 and out of the orifice 34. The one-way valve 64 may be composed of various materials. Examples of such material includes, but is not limited to, silicone, polyvinylchloride (PVC), polyurethane, polyether urethane, polyether urethane urea, polyamide, polyacetal, polyester, poly ethylene-chlorotrifluoroethylene, poly tetrafluoroethylene (PTFE or "Teflon®"), styrene butadiene rubber, polyethylene, polypropylene, polyphenylene oxide-polystyrene, poly-a-chloro-p-xylene, polymethylpentene, polysulfone and other related biostable polymers. In fact, one-way valve 64 may be made of the same material as the earplug 14 and may additionally be molded with the earplug 14 as the earplug 14 is molded.

As mentioned above, more than one one-way valve 64 may be located along the lumen 24. In this configuration of multiple one-way valves 64, the one-way valves 64 may be of the same type or of different types. Further, the one-way valves 64 may be of different sizes, shapes, flow rates, opening pressures or other physical or functional properties.

In use, the delivery bulb 16 is first filled with treatment fluid 12. This may be accomplished in many ways. The delivery bulb 16 could be pre-filled with a desired treatment fluid 12 and then attached to the earplug 14 as described above. Or, the delivery bulb 16 could be separated from the earplug 14, turned so that the open distal end 38 of the delivery bulb 16 is facing upwards, and treatment fluid 12 poured from a container or injected from a syringe, dropper or spigot into the delivery bulb 16 through the open distal end 38. Other ways of filling the delivery bulb 16 with treatment fluid 12 may occur to those skilled in that art and are intended to be included in the use of the device 10.

Figure 8:
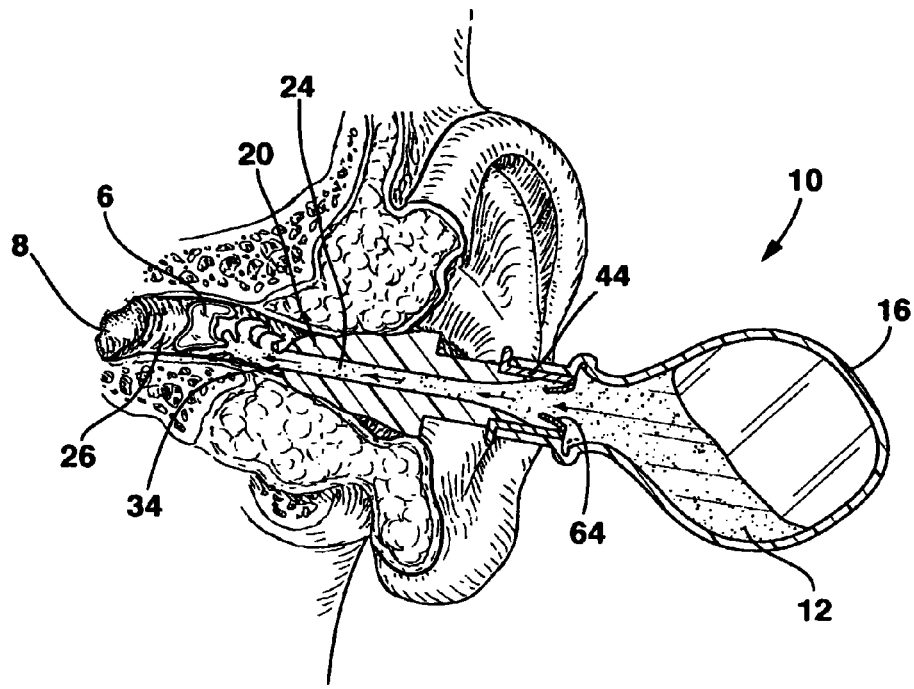
FIG. 8 is a cross-sectional view of the embodiment of FIG. 1 in use in a patient's ear.
Figure 9:
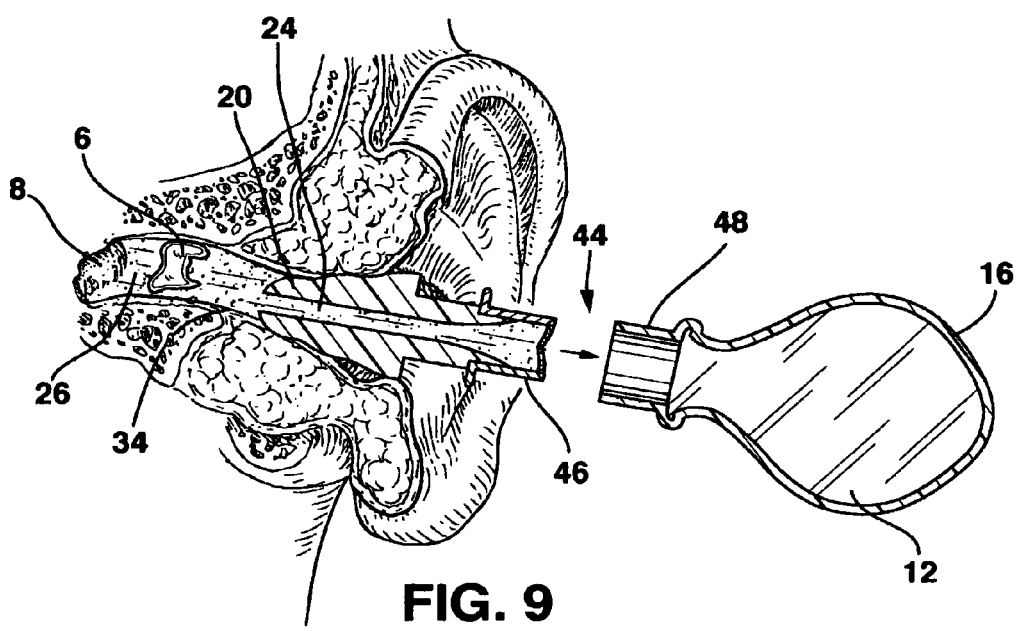
FIG. 9 is a cross-sectional view of the embodiment of FIG. 1 in use in a patient's ear with the bulb separated from the stem.

With treatment fluid 12 in the delivery bulb 16, the distal end 18 of the earplug 14 is inserted into the patient's external ear canal 26 as shown in FIG. 8. Treatment fluid 12 contained within the delivery bulb 16 is dispensed by squeezing the delivery bulb 16 thereby releasing the treatment fluid 12 through the lumen 24 and orifice 34 into the external ear canal 26. Once the treatment fluid 12 is dispensed into the external ear canal 26, the empty delivery bulb 16 may be separated from and removed from the earplug 14 by separating the channel 46 from the sleeve 48 (FIG. 9) or the channel 50 from the sleeve 52 or by whatever appropriate means the attachment mechanism 44 provides, as is well understood in the art.

The inserted earplug 14 with its one-way valve 64 prevents the treatment fluid 12 or cleansing solution from draining out of the external ear canal 26, thus allowing the entrapped treatment fluid 12 to remain in the external ear canal 26 for a desired period of time. The earplug 14 is then removed from the external ear canal 26 allowing the resulting mixture of treatment fluid 12 and wax debris or waste fluid 28 to drain out of the ear by gravity.

In embodiments of the device 10 represented in FIGS. 10-13, the device 10 includes a collection tube 66 and a collection reservoir 68. Collection tube 66 is a hollow tube preferably located in earplug 14 that extends from a collection orifice 70 to the collection reservoir 68. Collection orifice 70 is preferably, but not required to be, located near the distal end 18 of earplug 14. Alternately, collection tube 66 can be located in whole or in part on the outside of the outer surface 22 of the earplug 14.

The function of collection reservoir 68 is to collect waste treatment fluid 72. Waste treatment fluid 72 is treatment fluid 12 that has already been injected into the patient's external ear canal 26 and which may also include earwax or other debris from the patient's external ear canal 26. Because the function of collection reservoir 68 is to collect waste treatment fluid 72, collection reservoir 68 need only be able to receive and contain the waste treatment fluid 72. Consequently, in the preferred embodiment the collection reservoir 68 is a flexible bag such as a bag made of flexible rubber, soft thermoplastic material such as vinyl or a silicon elastomer. Alternately, collection reservoir 68 could be made of a somewhat more rigid material such as polyester but of a reduced thickness or of a bellows configuration. In either of these form a, the collection reservoir 68, when empty, is collapsed and when full, expands to hold the waste treatment fluid 72.

In the embodiment, shown in FIG. 10, the collection reservoir 68 is directly attached to the earplug 14 and collection tube 66 fluidly connects the collection reservoir 68 to the collection orifice 70. In this embodiment, the collection tube 66 terminates in a collection reservoir connection fitting 78. The function of collection reservoir connection fitting 78 is to fluidly connect the collection reservoir 68 to the earplug 14 through the collection tube 66.

Once again, it is well known how to connect tubing such as the collection tube 66 to a reservoir such as the collection reservoir 68. Consequently, there is an almost limitless number of ways to accomplish this connection. One configuration of collection reservoir connection fitting 78 is for earplug 14 to include a collection reservoir attachment lip 80 located near the proximal end 20 of earplug 14. In the preferred embodiment, collection reservoir attachment lip 80 is a branch formed near the proximal end 20 of earplug 14 that extends away from earplug 14 at an angle. Collection reservoir 68 has a sleeve 82 mode of an extension of the material of collection reservoir 68 that fits into and around connection reservoir attachment lip 80 to sealingly connect collection reservoir 68 to collection tube 66 and hence to earplug 14. In these embodiments with the collection reservoir 68, the earplug 14 has both a lumen 24 and a collection tube 66. There are many well known ways to have dual lumens in devices. One such way is shown in FIG. 11 where the lumen 24 and the collection tube 66 lie within the earplug 14 in a side-by-side configuration. Another way to have lumen 24 and collection tube 66 in the earplug is shown in FIG. 12 where the collection tube 66 partially surrounds the lumen 24 (or vice versa).

In an alternate embodiment, shown in FIG. 13, the collection reservoir 68 is located remote from the earplug 14. In this embodiment, the collection reservoir 68 is also attached to the collection orifice 70 of earplug 14 through the collection tube 66. But, a hollow conduit 84 connects the collection tube 66 to the collection reservoir 68 so that waste treatment fluid 72 may be collected from the area distal to the distal end 18 of the earplug 14 through the collection orifice 70 and passed through the collection tube 66 and hollow conduit 84 to the collection reservoir 68.

Collection tube 66 in this embodiment may also include a pinch valve 86 located along collection tube 66 preferably near the end of the collection tube 66 near earplug 14. The function of pinch valve 86 is to open or close the collection tube 66 to the passage of waste treatment fluid 72. Consequently, pinch valve 86 may take any of a number of forms well-known in the art. Pinch valve 86 is opened when it is desired for waste treatment fluid 72 to pass from the earplug 14 to the collection reservoir 68 but may be closed when collection tube 66 is separated from the earplug 14, as for example, at the end of the therapeutic session, to prevent spillage of waste treatment fluid 72 from the collection tube 66.

In the embodiments of device 10 having a collection reservoir 68, collection reservoir 68 may aid in the retrieval of waste treatment fluid 72. This is preferably accomplished by collection reservoir 68 providing a slight vacuum to pull the waste treatment fluid 72 into the collection orifice 70, through the collection tube 66 (and through the hollow conduit 84, if present) into the collection reservoir 68. In this embodiment, instead of collection reservoir 68 being made of a flexible material, collection reservoir 68 is made of a material such as vinyl or a rubber compound that allows the collection reservoir 68 to expand as fluid is placed into or drawn into the collection reservoir 68. Preferably, the material and thickness of collection reservoir 68 is such that when collection reservoir 68 is squeezed and then released, collection reservoir 68 on its own will return to its un-squeezed or un-compressed condition and in the process of doing so, draw a vacuum that helps to draw the waste treatment fluid 72 into the collection reservoir 68.

Figure 14:
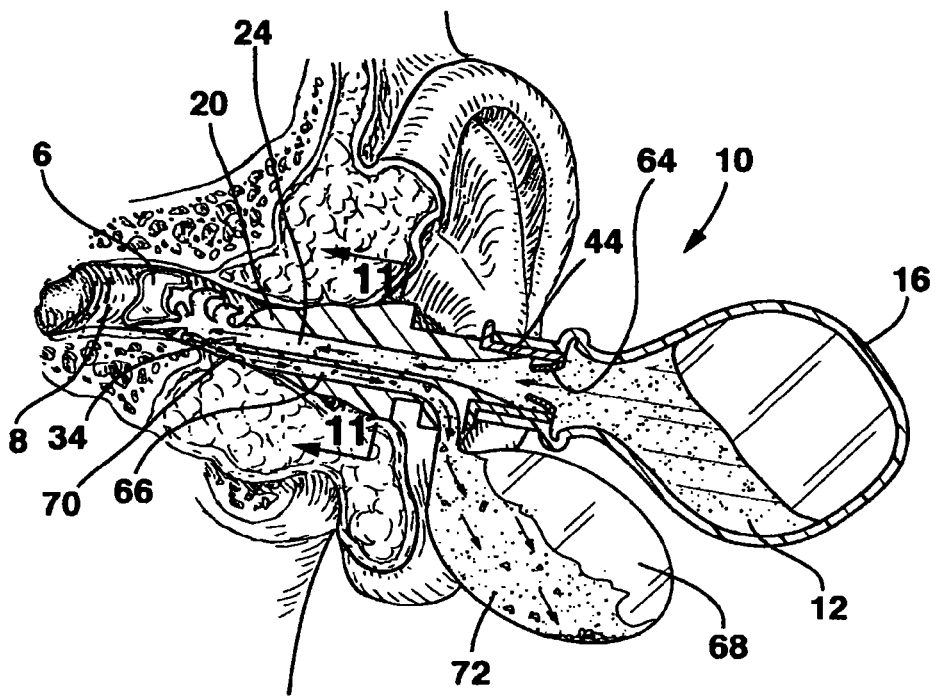
FIG. 14 is a side cross-sectional view of the embodiment of FIG. 10 in use in a patient's ear.

In these embodiments having a collection reservoir 68 as well, as shown in FIG. 14, the earplug 14 is placed in the patient's external ear canal 26 and treatment fluid 12 is dispensed from the delivery bulb 16 into the external ear canal 26 through lumen 24 in earplug 14. The resulting mixture of treatment fluid 12 and earwax debris or waste treatment fluid 12 drains out of the external ear canal 26 through the collection tube 66 contained within the earplug 14 and into the collection reservoir 68 connected to the earplug 14. The collection reservoir 68 containing the waste treatment fluid 72 may then be discarded.

Figure 15:
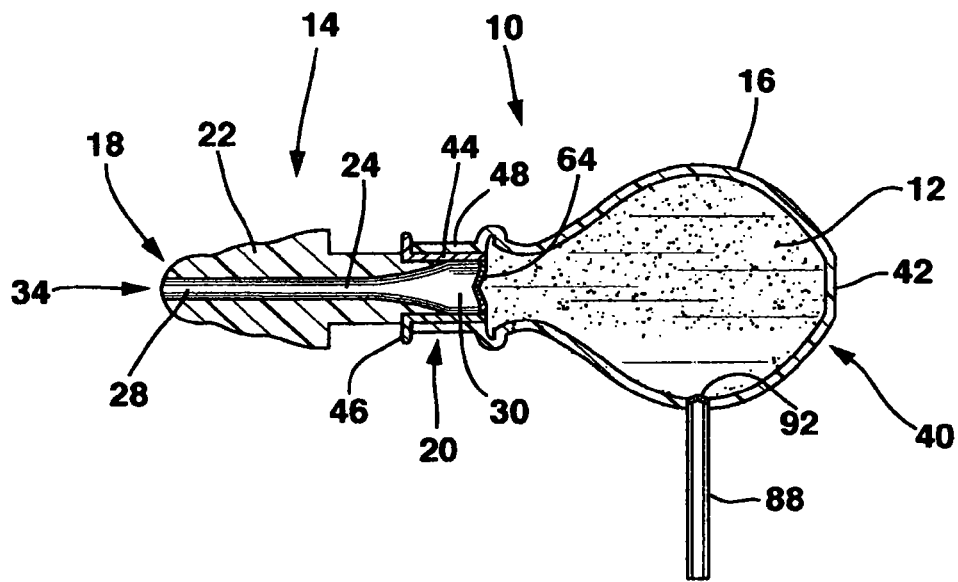
FIG. 15 is a side cross-sectional view of an alternate embodiment of the invention of FIG.

In use, the delivery bulb 16 may be preloaded with treatment fluid 12 and attached to the earplug 14 as described above. Alternately, as shown in FIG. 15, the delivery bulb 16 may be attached to the earplug 14 without any treatment fluid 12 in the delivery bulb 16. In this case, delivery bulb 16 includes a pre-fill stem 88 with a distal end 90 and a one-way valve 92. Pre-fill stem 88 is a conduit fluidly connected to the delivery bulb 16 so that treatment fluid 12 can pass into the pre-fill stem 88 at distal end 90 and travel through the pre-fill stem 88 to the delivery bulb 16. Pre-fill stem 88 may be located anywhere on delivery bulb 16. In addition, pre-fill stem 88 may be made of the same material as delivery bulb 16 and in fact may be molded with delivery bulb 16 together with delivery bulb 16 as delivery bulb 16 is being molded.

One-way valve 92 is located either within pre-fill stem 88 or at the point where pre-fill stem 88 attaches to the delivery bulb 16. One-way valve 92 allows fluid to flow only in a direction from the distal end 90 of pre-fill stem 88 to the delivery bulb 16. As such, one-way valve 92 can take many forms so long as fluid, such as treatment fluid 12, is allowed to pass through one-way valve 92 to, but not out of, the delivery bulb 16. Examples of valves appropriate for one-way valve 92 include, but are not limited to, slit valves, check valves including swing valves (monocuspid, bicuspid, tricuspid), lift valves, ball valves, tilting disk valves, dual plate (leaflet) valves, diaphragm valves, flap valves and general valves including ball valves, butterfly valves, check valves, diaphragm valves, gate valves, globe valves, plug valves, duck bill valves and pinch valves. In one embodiment, one-way valve 92 may be made of the same material as either the delivery bulb 16 or prefill stem 88 or both and may be molded together with either the delivery bulb 16, pre-fill stem 88 or both as the delivery bulb 16 or pre-fill stem 88 are molded.

In this embodiment, to fill delivery bulb 16, treatment fluid 12 is added to the delivery bulb 16 by compressing the delivery bulb 16 to expel air out of the delivery bulb 16 through lumen 24 past one-way valve 64. Then, while the delivery bulb 16 is still compressed, the distal end 90 of pre-fill stem 88 is placed in a container of treatment fluid 12. Thereafter, delivery bulb 16 is released where the material of delivery bulb 16 causes it to return to its uncompressed condition. As delivery bulb 16 returns to its uncompressed condition, it draws a vacuum that sucks the treatment fluid 12 through the pre-fill stem 88 past the one-way valve 92 into the delivery bulb 16.

Figure 16:
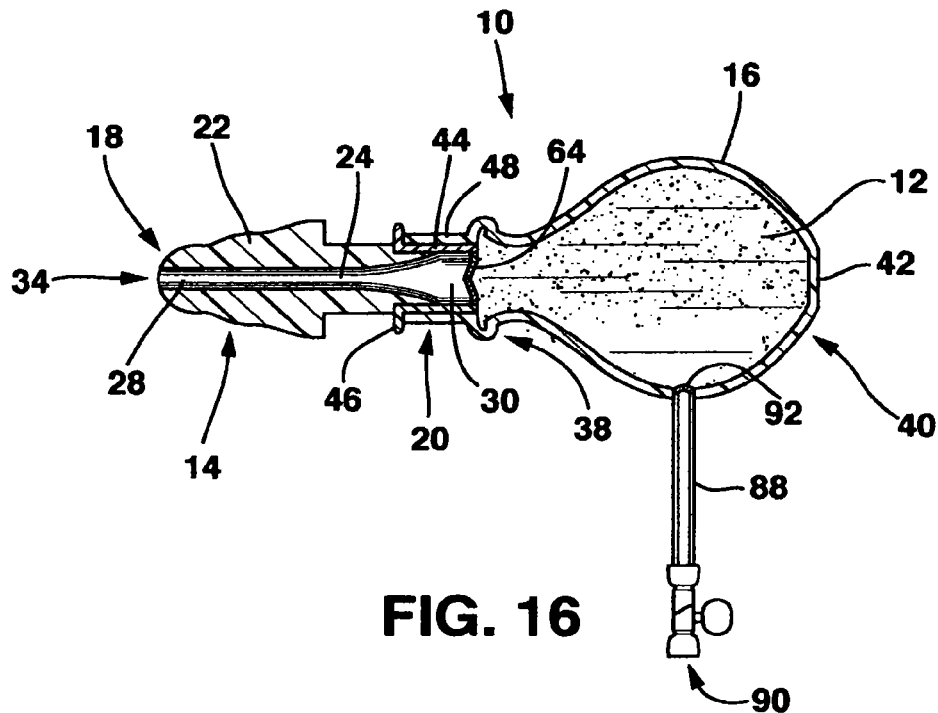
FIG. 16 is a side cross-sectional view of an alternate embodiment of the invention of FIG. 15.

In a slight variant of this embodiment shown in FIG. 16, the distal end 90 of the pre-fill stem 88 has a luer connector 94 that may be mated to another luer connector on, for example, a bag of treatment fluid 12 or a syringe filled with treatment fluid 12. In this way, treatment fluid 12 can be transferred from a gross storage container into the delivery bulb 16 to be delivered to the patient as described herein.

Figure 17:
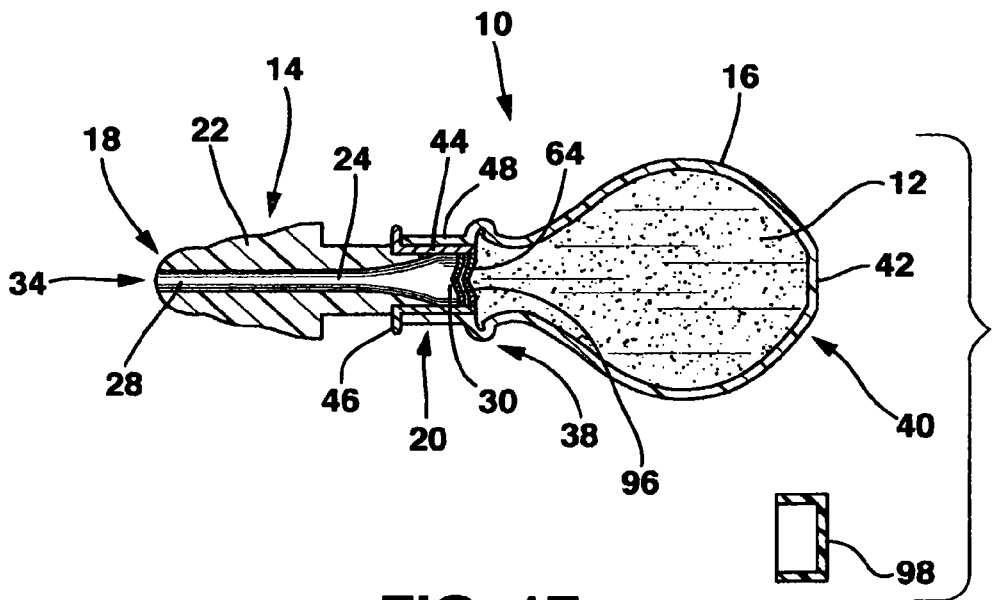
FIG. 17 is a side cross-sectional view of an alternate embodiment of the invention.

In another embodiment of the invention shown in FIG. 17, the delivery bulb 16 has a one-way valve 96 located at its distal end 38 near the connection point to the earplug 14. One-way valve 96 is preferably a valve of the type that opens under pressure but remains closed otherwise. In this way, one-way valve 96 allows treatment fluid 12 to pass out of the delivery bulb 16 when the delivery bulb 16 is squeezed to send the treatment fluid to the earplug 14 but prevents any treatment fluid 12 remaining in the delivery bulb 16 from escaping from the delivery bulb 16 when the delivery bulb 16 is separated from the earplug 14. Examples of one-way valve 96 include, but are not limited to, slit valves, check valves including swing valves (monocuspid, bicuspid, tricuspid), lift valves, ball valves, tilting disk valves, dual plate (leaflet) valves, double check valves, diaphragm valves, flap valves and general valves including ball valves, butterfly valves, check valves, diaphragm valves, gate valves, globe valves, plug valves, foot valves, duck bill valves and pinch valves. It is clear that many valve types may be used as one-way valve 96 including some not listed here. It is intended that any one-way valve that will occur to those skilled in the art that prevents treatment fluid 12 from escaping from the delivery bulb 16 when the delivery bulb 16 is separated from the earplug 14 may be used for one-way valve 96.

Further, this configuration allows, but does not require, that the one-way valve 64 in the lumen 24 of earplug 14 may be eliminated and replaced with a cap 98 attachable by frictional fit, mechanical connection or threads to the proximal end 30 of lumen 24. The function of cap 98 is to close the proximal end 30 of lumen 24 once the treatment fluid 12 has been delivered to the patient's external ear canal 26 and the delivery bulb 16 separated from the earplug 14. Except as described above, in all other ways, the device 10 in the embodiment, including all the embodiments and variations associated with the earplug 14 are as described above. Specifically, this embodiment of the delivery bulb 16 may be used with any embodiment of the device 10 above including embodiments with one-way valve 64 in lumen 30.

Figure 18:
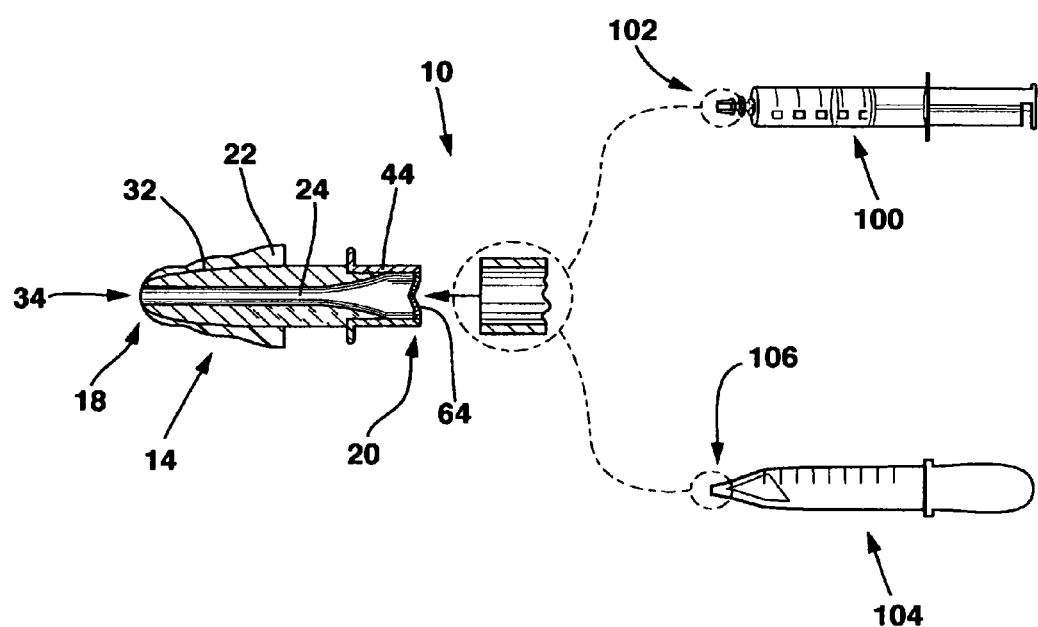
FIG. 18 is a side cross-sectional view of another alternate embodiment of the invention.

It is also intended that the device 10, in an embodiment shown in FIG. 18, be used with a syringe 100 such as is common in doctors' offices. In this embodiment, the distal end 102 of the syringe 100 is mated to the proximal end 20 of earplug 14. To accomplish this, the distal end 102 of the syringe 100 may be a common luer connection with the proximal end 20 of earplug 14 formed as the corresponding luer connection. Alternately, the material of the proximal end 20 of earplug 14 may be extended to form an opening into which the distal end 102 of the syringe 100 may securely and sealingly fit in a male-female relationship. Other means for securing the distal end 102 of the syringe 100 to the proximal end 20 of the earplug 14 will occur to those skilled in the art. Any such means are intended to be included in the design of the device 10 in this embodiment so long as the distal end 102 of the syringe 100 is securely, fluidly and sealingly mated to the proximal end 20 of the earplug 14. In this way, the syringe 100 can be filled with treatment fluid 12 as is common for such syringes or pre-filled with treatment fluid 12, as for example by a third party and supplied as such, and stored for later use.

In either variant, when it is desired to use the device 10 and therefore supply treatment fluid 12 to the device 10, the syringe 100 is connected to the earplug 14 as described. Thereafter, the plunger mechanism on the syringe 100 is activated to move treatment fluid 12 from the syringe 100 to the earplug 14 to exit the earplug 14 at the orifice 34 as described above.

It is also intended in another embodiment of the device 10 shown in FIG. 18, that the device 10 be used with an ear dropper 104 such as is common in doctors' offices and at homes. In this embodiment, the distal end 106 of the ear dropper 104 is mated to the proximal end 20 of earplug 14. To accomplish this, the distal end 106 of the ear dropper 104 may be changed to form a common luer connection and the proximal end 20 of earplug 14 is formed with the corresponding luer connection. Alternately, the material of the proximal end 20 of earplug 14 may be extended to form an opening into which the distal end 106 of the common ear dropper 104 may securely, sealingly and frictionally fit in a male-female relationship. Other means for securing the distal end 106 of the ear dropper 104 to the proximal end 20 of the earplug 14 will occur to those skilled in the art. Any such means are intended to be included in the design of the device 10 in this embodiment so long as the distal end 106 of the ear dropper 104 is securely, fluidly and sealingly mated to the proximal end 20 of the earplug 14. In this way, the ear dropper 104 can be filled with treatment fluid 12 as is common for such ear droppers or pre-filled with treatment fluid 12, as for example by a third party and supplied as such, and stored for later use.

In either variant, when it is desired to use the device 10 and therefore supply treatment fluid 12 to the device 10, the ear dropper 104 is connected to the earplug 14 as described. Thereafter, the bulb of the ear dropper 104 is squeezed to move treatment fluid 12 from the ear dropper 104 to the earplug 14 to exit the earplug 14 at the orifice 34 as described above.

In all the embodiments shown above, a delivery bulb 16 holds the therapeutic treatment fluid 12 for delivery to the earplug 14. In an embodiment shown schematically in FIG. 19, the treatment fluid 12 is stored in a reservoir 108 that is connected to a pump 110 that is in turn connected to the earplug 14 through a tube 112 that fluidly connects the pump 110 to the lumen 24. Pump 110 moves the treatment fluid 12 from the reservoir 108 through tube 112 and lumen 24 to the orifice 34 where the treatment fluid 12 exits the earplug 14 as described above. In this embodiment as well, a one-way valve 64 is again preferably placed within the lumen 24 in earplug 14 to prevent treatment fluid 12 from escaping the lumen 24 when the tube 112 is disconnected from either the earplug 14. As a result, earplug 14 may receive treatment fluid 12 from the reservoir 108 but allow the earplug 14 to be separated from the reservoir 108 and pump 110 preferably at the connection between the earplug 14 and the tube 112.

However, an additional one-way valve 114 may also be placed along tube 112, preferably near where the tube 112 connects to the earplug 14, to prevent spillage of treatment fluid 12 from tube 112 when tube 112 is separated from the earplug 14. Further, a one-way valve 116 may be placed within tube 112 near where tube 112 connects to the pump 110 to prevent spillage of treatment fluid 12 out of the tube 112 if tube 112 is separated from the pump 110. Another one-way valve or control valve 118 may be placed in pump 110 near where pump 110 connects to the tube 112 so that treatment fluid 12 will not spill from the pump 110 should the tube 112 be disconnected from the pump 110. It is clear in this embodiment that one-way valves 106, 108 and 118 may be used individually or in any combination. Further, one-way valves 106, 108 and 118 may be of the same type or of different types. In addition, the one-way valves 106, 108 and 118 may be of different sizes, shapes, flow rates, opening pressures or other physical or functional properties.

Figure 19:
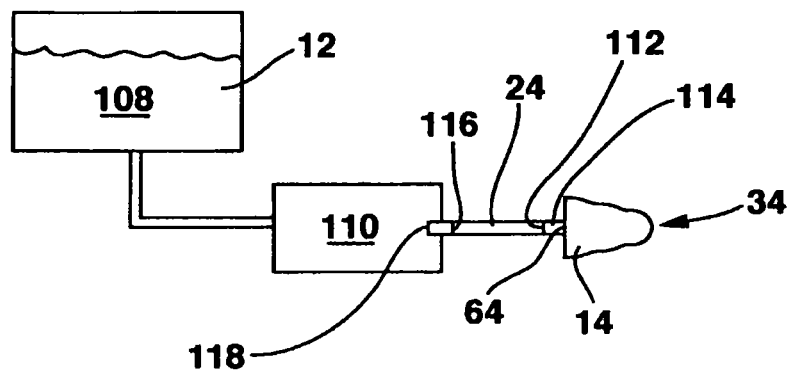
FIG. 19 is a schematic diagram of an alternate embodiment of the invention.
Figure 20:
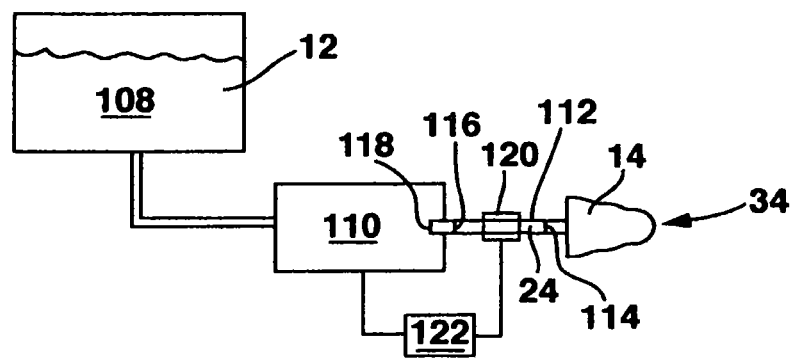
FIG. 20 is a schematic diagram of a variant of the embodiment of FIG. 19.

FIG. 20 shows a slight variant of the device 10 of FIG. 19. In this variant, a pressure sensor 120 is placed in contact with tube 112 or pump 110 to sense the pressure provided by the tube 112 to the earplug 14. Pressure sensor 120 is connected to a control circuit 114 that may be a microprocessor, application specific integrated circuit (ASIC) or discrete components that respond to the pressure sensed by the pressure sensor 120 to produce a control signal for operating the pump 110. If the pressure is too high, pump 110 is directed by control circuit 114 to adjust itself to reduce the pressure. Conversely, if the pressure is too low, control circuit 114 directs the pump 110 to adjust itself to increase the pressure.

In the embodiments of both FIGS. 18 and 19, the device 10 includes an earplug 14 in all the various embodiments described including with or without collection reservoir 68.

The device 10 described above in all its various embodiments and variants may be applied to a multitude of ear care or therapeutic tasks. For example, the device 10 may be used for earwax irrigation, to deliver treatment fluids 12 to the patient's external ear canal 26 for a therapeutic benefit or to cleanse the external ear canal 26, or to deliver treatment fluids 12 to the middle ear through a tympanostomy or ear drum perforation such as in the case of a middle ear infection (otitis media) or to dispense ear pain relieving fluid solutions (as in the case of external ear canal inflammation as well as in a middle ear infection).

In any of these situations the delivery bulb 16 may be preloaded with the specific treatment fluid 12 or it can be refilled for each particular use. In the embodiments where the delivery bulb 16 is preloaded with treatment fluid 12, the delivery bulb 16 is manufactured separately or separated from the earplug 14, the delivery bulb 16 is filled with the desired treatment fluid 12 and the delivery bulb 16 re-attached to the earplug 14 with the delivery bulb 16 filled as described above. Thereafter, the distal end 18 of the earplug 14 is placed in the patient's external ear canal 26 until the outer body 22 of the earplug 14 forms a sealing fit with the patient's external ear canal 26. When a seal is formed between the earplug 14 and the patient's external ear canal 26, the delivery bulb 16 is squeezed whereby the treatment fluid 12 is forced past the one-way valve 64, through the lumen 24 and out of the orifice 34 into the space in the patient's external ear canal 26 between the distal end 46 of the earplug 14 and the patient's eardrum 8. It may be desirable to place a pressure-relief valve on the delivery bulb 16 or along the lumen 24 or both to prevent the inadvertent application of too high of a pressure of the treatment fluid 12 to the patient's external ear canal 26 or eardrum 8.

The one-way valve 64 prevents the treatment fluid 12 from leaving the area distal to the distal end 18 of the earplug 14 and reentering the delivery bulb 16 through the earplug 14. Further, in the embodiments where the delivery bulb 16 is removed from the earplug 14, the delivery bulb 16 may be removed from the earplug 14 so that the one-way valve 64 forms a closure that keeps the treatment fluid 12 in the earplug 14 and the patients external ear canal 26 in contact with the patient's middle ear 26 and eardrum 8 for a therapeutically useful time period.

When it is desirable to remove the treatment fluid 12 from the patient's external ear canal 26, in the embodiment where there is a collection reservoir 68, the user releases or removes the pinch valve 86 if present and collapses the collection reservoir 68 to draw a vacuum to draw the waste treatment fluid 72 out of the patient's external ear canal 26 or just lets the waste treatment fluid 72 drain into the collection reservoir 68. Again, it may be desirable to include a pressure relief valve along the collection tube 66 or at the collection reservoir 68 or both to prevent drawing too high a vacuum with the possible concomitant result of damaging the patient's external ear canal 26 or eardrum 8.

In the embodiment where there is no collection reservoir 68, the earplug 14 is removed from sealing contact with the patient's external ear canal 26 whereupon the now waste treatment fluid 72 drains from the patient's external ear canal 26 to be removed by, for example, a towel.

A part of the invention is to use the device 10 to treat treating maladies of the external ear canal 26 and eardrum 8 including by supplying treatment fluids 12 to the external ear canal 26 and to and through the eardrum 8 where a tympanostomy tube is present. Consequently, methods for treating such maladies are disclosed. Examples of specific maladies that can be treated with the device 10 described herein are disclosed. However, these examples are intended to be illustrative and not limiting. It is clear that the device 10 disclosed can be used to deliver treatment fluids 12 as described herein for many therapies as will be clear to those skilled in the art.

To treat otalgia, otitis media, otitis externa, post tympanostomy tube otorrhea and otorrhea with tympanic membrane perforation, in the embodiments using a delivery bulb 16, the delivery bulb 16 is either preloaded with the specific treatment fluid 12 of choice (e.g., water, antibiotics, anti-inflammatory agents, or dehydrating solution) or, in the embodiments described that allow the treatment fluid 12 to be drawn into the delivery bulb 16, the specific treatment fluid 12 of choice is drawn into the delivery bulb 16. In the embodiments using a reservoir 108, the specific treatment fluid 12 of choice is placed in the reservoir 108.

In any case, the earplug 14 is placed into the patient's external ear canal 26 so that the portions of the outer body 22 nearer the proximal end 20 of the earplug 14 comes into sealing contact with the patient's external ear canal 26. Because body 22 is somewhat pliable, it will conform to the shape of the patient's external ear canal 26 as the earplug 14 is placed in the patient's external ear canal 26.

In the embodiments using a delivery bulb 16, the delivery bulb 16 is squeezed to send the treatment fluid 12 to the earplug 14 through one-way valve 96 and lumen 24 to exit the device 10 through orifice 34 where the treatment fluid 12 comes into therapeutic contact with the tissue of the external ear canal 26 or eardrum 8. The sealing contact between the body 22 and the patient's external ear canal 26 retains the treatment fluid 12 in this therapeutic contact with the tissue. In the embodiments using a reservoir 108, the pump 110 is activated to send the treatment fluid to and through the earplug 14 and out the orifice 34.

In the embodiments having a collection tube 66 and a collection reservoir 68, collection reservoir 68 is preferably compressed prior to the user inserting the earplug 14 into the patient's external ear canal 26 and the pinch valve 86 closed. In this way, a slight vacuum tendency of the collection reservoir 68 as it attempts to return to its uncompressed state is preserved. When the user desires to remove the waste treatment fluid 72 from the patient's external ear canal 26, the pinch valve 86, if present, is opened and collection reservoir 68 provides a slight vacuum as it rectums to its unstressed condition to pull the waste treatment fluid 72 into the collection orifice 70, through the collection tube 66 (and through the hollow conduit 84, if present) into the collection reservoir 68. The collection reservoir 68 containing the waste treatment fluid 72 may then be discarded or the waste treatment fluid 72 drained from the collection reservoir 68 and discarded.

To treat cerumen otic impaction, in the embodiments using a delivery bulb 16, the delivery bulb 16 is either preloaded with the specific treatment fluid 12 of choice (e.g., water, hydrogen peroxide, mineral oil, baby oil, Burrow's solution, or any other biologically compatible fluid that irrigates or moisturizes the external ear canal 26 or breaks down or dissolves cerumen) or, in the embodiments described that allow the treatment fluid 12 to be drawn into the delivery bulb 16, the specific treatment fluid 12 of choice is drawn into the delivery bulb 16. In the embodiments using a reservoir 108, the specific treatment fluid 12 of choice is placed in the reservoir 108.

In any case, the earplug 14 is placed into the patient's external ear canal 26 so that the portions of the outer body 22 nearer the proximal end 20 of the earplug 14 comes into sealing contact with the patient's external ear canal 26. Because body 22 is somewhat pliable, it will conform to the shape of the patient's external ear canal 26 as the earplug 14 is placed in the patient's external ear canal 26.

In the embodiments using a delivery bulb 16, the delivery bulb 16 is squeezed to send the treatment fluid 12 to the earplug 14 through one-way valve 96 and lumen 24 to exit the device 10 through orifice 34. It may be desirable to direct the treatment fluid 12 onto areas in the patient's external ear canal 26 where the cerumen is located to use the physical contact between the treatment fluid 12 and the cerumen to help dislodge the cerumen. In this case, it may be desirable to use an earplug 14 with an orifice 34 located along the surface of the outer body 22 away from the ultimate distal end 18 of earplug 14 but still before the part of outer body 22 that contacts and provides a seal with the patient's external ear canal 26 (FIG. 4). The sealing contact between the body 22 and the patient's external ear canal 26 retains the treatment fluid 12 in this therapeutic contact with the tissue. In the embodiments using a reservoir 108, the pump 110 is activated to send the treatment fluid to and through the earplug 14 and out the orifice 34.

In the embodiments having a collection tube 66 and a collection reservoir 68, collection reservoir 68 is preferably compressed prior to the user inserting the earplug 14 into the patient's external ear canal 26 and the pinch valve 86 closed. In this way, a slight vacuum tendency of the collection reservoir 68 as it attempts to return to its uncompressed state is preserved. When the user desires to remove the waste treatment fluid 72 from the patient's external ear canal 26, the pinch valve 86, if present, is opened and collection reservoir 68 provides a slight vacuum as it returns to its unstressed condition to pull the waste treatment fluid 72 into the collection orifice 70, through the collection tube 66 (and through the hollow conduit 84, if present) into the collection reservoir 68. The collection reservoir 68 containing the waste treatment fluid 72 may then be discarded or the waste treatment fluid 72 drained from the collection reservoir 68 and discarded.

The present invention has been described in connection with certain embodiments and dimensions. It is to be understood, however, that the description given herein has been given for the purpose of explaining and illustrating the invention and are not intended to limit the scope of the invention. For example, as is well understood in the art, it is clear that a near infinite number of manners of connecting the delivery bulb 16 to the earplug 14 or each of these to tube 32 may be used. It is not intended that the invention be limited to the specific designs shown. Rather, the invention is intended to encompass the elements disclosed and their functional equivalents interacting as described herein.

Further, the present invention has been described in connection with devices and methods for treating maladies of the external ear canal, middle ear and eardrum and more particularly to such devices and methods that supply treatment fluids to the external ear canal and into the middle ear through the eardrum where a tympanostomy tube or a perforation is present. However, it is within the scope of the invention to provide devices 10, as described herein, for delivering treatment fluid to other body orifices or cavities. For example, for the purpose of illustration and not by way of limitation, the following are a few examples of uses of the device 10 in other body cavities and orifices:

1. Rectal applications such as in enema flushes, hemorrhoid medication insertion and other types of solutions that are known by those skilled in the art to be applied into and through the anorectal area The device 10 may also be used for the injection of contrast material into the colon such as used in barium enemas.

2. Nasal irrigation and instillation of nasal solutions such as antibiotics, antifungals, decongestants and other solutions known by those skilled in the art to be administered to the nose, nasal passages or sinuses.

3. Urologic applications including the injection of urinary irrigation solutions, contrast dye, antibiotics and other medications known by those skilled in the art that are delivered into the urethra. In all of the above listed applications of the device 10, a common goal is the delivery of a therapeutic solution into a body orifice or cavity with the advantage of the device 10, as described in this specification, in preventing solution backflow, enabling an individual to be ambulatory and collecting of the used solution into a reservoir. Consequently, the device 10 in these and similar applications is substantially as described above with the exception that the earplug 14 is modified in size, shape and possibly other physical properties such as flexibility, rigidity and pliancy to become a plug 14' that accommodates forming a sealing fit with the orifice or body cavity to which it is applied.

The device 10 according to this embodiment of the invention is used to treat maladies of a patient's body orifice or body cavity by delivering a therapeutic solution into a body orifice or body cavity. This would be accomplished by providing a treatment fluid delivery device 10 comprising a delivery bulb 16 capable of holding a treatment fluid 12; a plug 14' removably connectable to the delivery bulb 16, the plug 14' having a distal end 18, a proximal end 20, an outer body 22 having an outer surface and a lumen 24 having a distal end 28 and a proximal end 30 wherein the lumen 24 terminates in an orifice 34 at the distal end 28 of the lumen 24, the proximal end 30 of the lumen 24 fluidly connected to the delivery bulb 16 so that treatment fluid 12 in the delivery bulb 16 may pass from the delivery bulb 16 to exit the plug 14' through the orifice 34, the plug 14' having a one-way valve 64 to prevent treatment fluid 12 from re-entering the delivery bulb 16 once treatment fluid 12 has left the delivery bulb 16, wherein the delivery bulb 16 may be removed from the plug 14' when the plug 14' is in position in a patient's body orifice or body cavity. Thereafter, a specific treatment fluid 12 of choice is placed into the delivery bulb 16. Then, the plug 14' is placed into a patient's body orifice or body cavity so that the portions of the outer body 22 nearer the proximal end 20 of the plug 14' come into sealing contact with the patient's body orifice or body cavity. The delivery bulb 16 is then squeezed to send the treatment fluid 12 to the plug 14' through the one-way valve 64 and the lumen 24 to exit the device 10 through the orifice 34 where the treatment fluid 12 comes into therapeutic contact with the tissue of the patient's body orifice or body cavity.

In a variant of this embodiment, the device 10 is used to treat maladies of a patient's body orifice or body cavity by delivering a therapeutic solution into a body orifice or body cavity by providing a treatment fluid delivery device comprising a reservoir 108 capable of holding a treatment fluid 12; a plug 14' removably connectable to the reservoir 108, the plug 14' having a distal end 18, a proximal end 20, an outer body 22 having an outer surface and a lumen 24 having a distal end 28 and a proximal end 30 wherein the lumen 24 terminates in an orifice 34 at the distal end 28 of the lumen 24, the proximal end 30 of the lumen 24 fluidly connected to the reservoir 108 so that treatment fluid 12 in the reservoir 108 may pass from the reservoir 108 to exit the plug 14' through the orifice 34, the plug 14' having a one-way valve 64 to prevent treatment fluid 12 from re-entering the reservoir 108 once treatment fluid 12 has left the reservoir 108, wherein the reservoir 108 may be removed from the plug 14' when the plug 14' is in position in a patient's body orifice or body cavity; and a pump 110 fluidly connected between the plug 14' and the reservoir 108 to move treatment fluid 12 from the reservoir 108 through the lumen 24 to the orifice 34 where the treatment fluid 12 exits the plug 14'. Thereafter, a specific treatment fluid 12 of choice is placed into the reservoir 108. Then, the plug 14' is placed into a patient's body orifice or body cavity so that the portions of the outer body 22 nearer the proximal end 20 of the plug 14' comes into sealing contact with the patient's body orifice or body cavity. The pump is then activated to send the treatment fluid 12 to the plug 14' through the one-way valve 64 and the lumen 24 to exit the device 10 through the orifice 34 where the treatment fluid 12 comes into therapeutic contact with the tissue of the patient's body orifice or body cavity.

In either method to treat maladies of a patient's body orifice or body cavity described above, the method further comprises providing a collection orifice 70, located near the distal end 18 of the plug 14; a collection reservoir 68; and a collection tube 66 connecting the collection reservoir 68 to the collection orifice 70, all substantially as described in this specification. In an alternate example embodiment, depicted in FIG. 21, the treatment delivery device 124 includes an ear canal engaging portion 126 integrally formed with an external portion 130, and defines an internal lumen 132 that extends through both. The ear canal engaging portion 126 is composed of a soft, molded, resilient material such as silicone, polyurethane, or another FDA-approved biocompatible material. Ear canal engaging portion 126 is dimensioned so that the distal end 128 may be placed into the external ear canal 26 of the patient. Moving proximally toward the external portion 130, the ear canal engaging portion 126 gradually increases in diameter until it merges with the external portion 130.

Spaced approximately equally along the length of the ear canal engaging portion 126 are minor disks 134, 136, and 138. The most distal minor disk 134 is located at or near the most distal end 128 of ear canal engaging portion 126. Minor disk 134 includes a proximal concave surface 142 and a distal convex surface 144. Proximal concave surface 142 is joined to distal convex surface 144 by a ridge 146.

Further proximally, ear canal engaging portion 126 presents a second minor disk 136. Minor disk 136 includes a proximal concave surface 148 and a distal convex surface 150. Proximal concave surface 148 is joined to distal convex surface 150 by a ridge 152. Additionally, minor disk 136 is slightly larger in diameter than minor disk 134.

Still further proximally, ear canal engaging portion 126 presents a third minor disk 138. Minor disk 138 includes a proximal concave surface 154 and a distal convex surface 156. Proximal concave surface 154 is joined to distal convex surface 156 by a ridge 158. Minor disk 138 is slightly larger in diameter than minor disk 136. Additionally, in an example embodiment, the distance between minor disk 134 and minor disk 136 is approximately equal to the distance between minor disk 136 and minor disk 138.

The proximal end of ear canal engaging portion 126 merges with external portion 130 of the treatment delivery device 124 to form one, unitary device. The external portion 130 includes major disk 140, an annular medication applicator receiving portion 160, and defines an internal lumen 132. The major disk 140 presents a proximal concave surface 162 and a distal convex surface 164. The proximal concave surface 162 and the distal convex surface 164 are joined by an intermediate member 166. Intermediate member 166 is a flat surface in this example. The major disk 140 is laterally offset from the internal lumen 132. The internal lumen 132 is joined to major disk 140 by the annular medication applicator receiving portion 160. The annular medication applicator receiving portion 160 is also formed of a soft, molded, resilient material such as silicone, polyurethane, or some other FDA-approved biocompatible material along with the rest of treatment delivery device 124. The annular medication applicator receiving portion 160 presents an annular ring 168, a first annular wall 164, and a second annular wall 166. The annular ring 168 has a flat surface. The proximal concave surface 162 is joined to the first annular wall 164 by a fillet 169. The internal lumen 132 is in fluid communication with the ear canal engaging portion 126.

Referring to FIG. 22, the wall of internal lumen 132 presents a first segment 172, a second segment 174, and a third segment 176 when cross-sectioned. The first segment 172 is located generally within minor disk 134 and has a generally frustoconical contoured shape.

Further proximally, the second segment 174 extends approximately between minor disk 134 and minor disk 136 and has a generally cylindrical shape. The second segment 174 presents a valve structure 178. The valve structure 178 includes a first leaflet 180 and a second leaflet 182. Each of leaflets 180 and 182 is shaped as half of a hemicylinders in this example embodiment. The planar surfaces along the longitudinal axes of leaflet 180 and leaflet 182 abut to form the valve structure 176. The leaflets 180 and 182 forming the valve structure 178 are made of an integrally molded, resilient material, consistent with that of the surrounding ear canal engaging portion 126. The resilient material allows the valve structure 178 to open in either direction under a preselected fluid pressure and close below the preselected fluid pressure, as depicted in FIGS. 23 and 24. The resilient material also allows for long-term therapeutic benefit by retaining the fluid in the treatment delivery device 124 for a desired period of time.

Still further proximally, the third segment 176 of internal lumen 132 begins at approximately the midpoint of minor disk 136 and continues through the annular medication applicator receiving portion 160. The third segment 176 also has walls defining a generally frustoconical shape. Third segment 176 has a chamfered edge 184 where it merges with second segment 174. At the proximal end of third segment 174 there is an annular indent 186 where it merges with the second annular wall 166. Although third segment 176 is generally frustoconical in shape it may also have a convex curvature 188 as depicted in FIG. 22.

Figure 25:
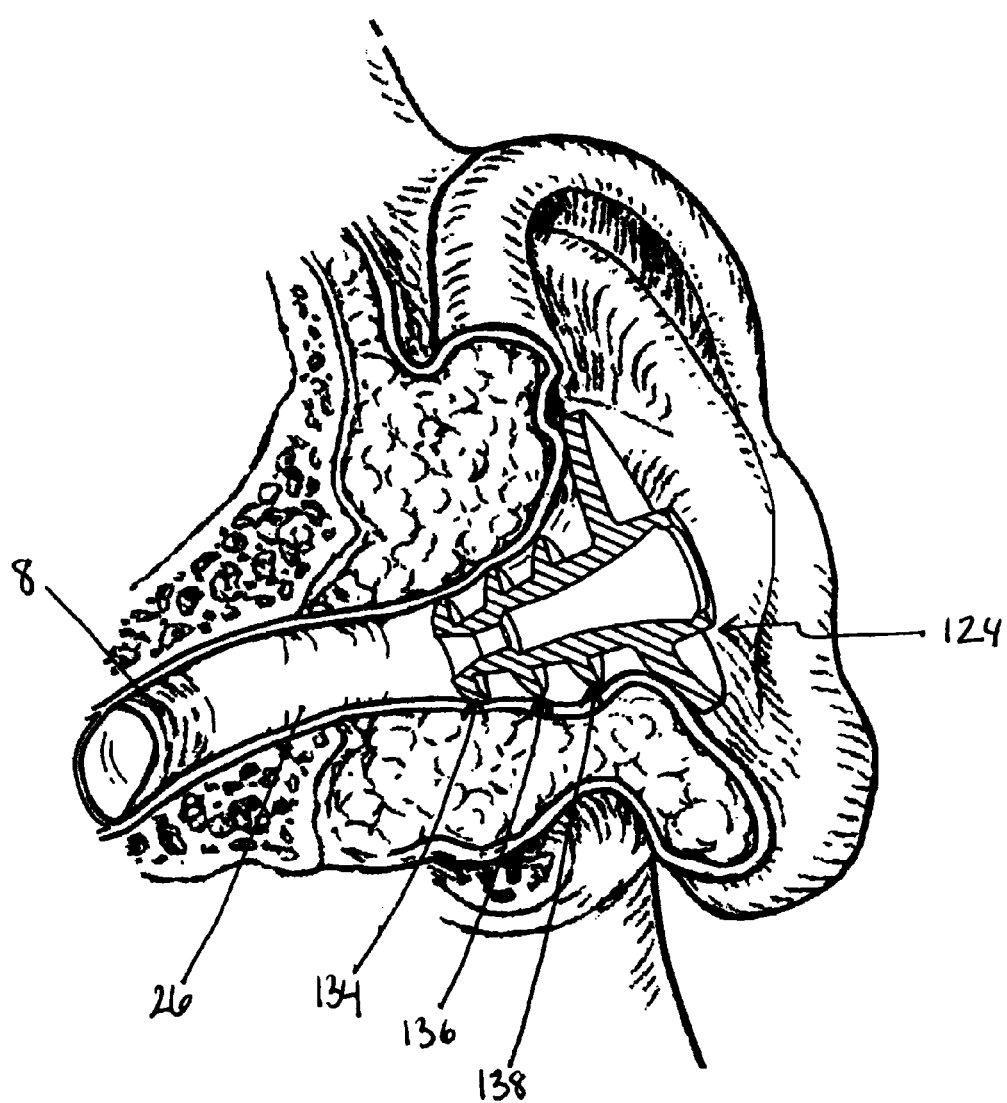
FIG. 25 is a cross-sectional view of the alternate embodiment of FIG. 21 positioned in a patient's ear.

Referring to FIG. 25, the treatment delivery device 124 is depicted in the external ear canal 26 of a patient. Also depicted is the eardrum 8 of the patient's ear (not to scale). The minor disks 134, 136, and 138 of treatment delivery device 124 are dimensioned such that they form a resilient seal with the wall of the external ear canal 26.

Figure 26:
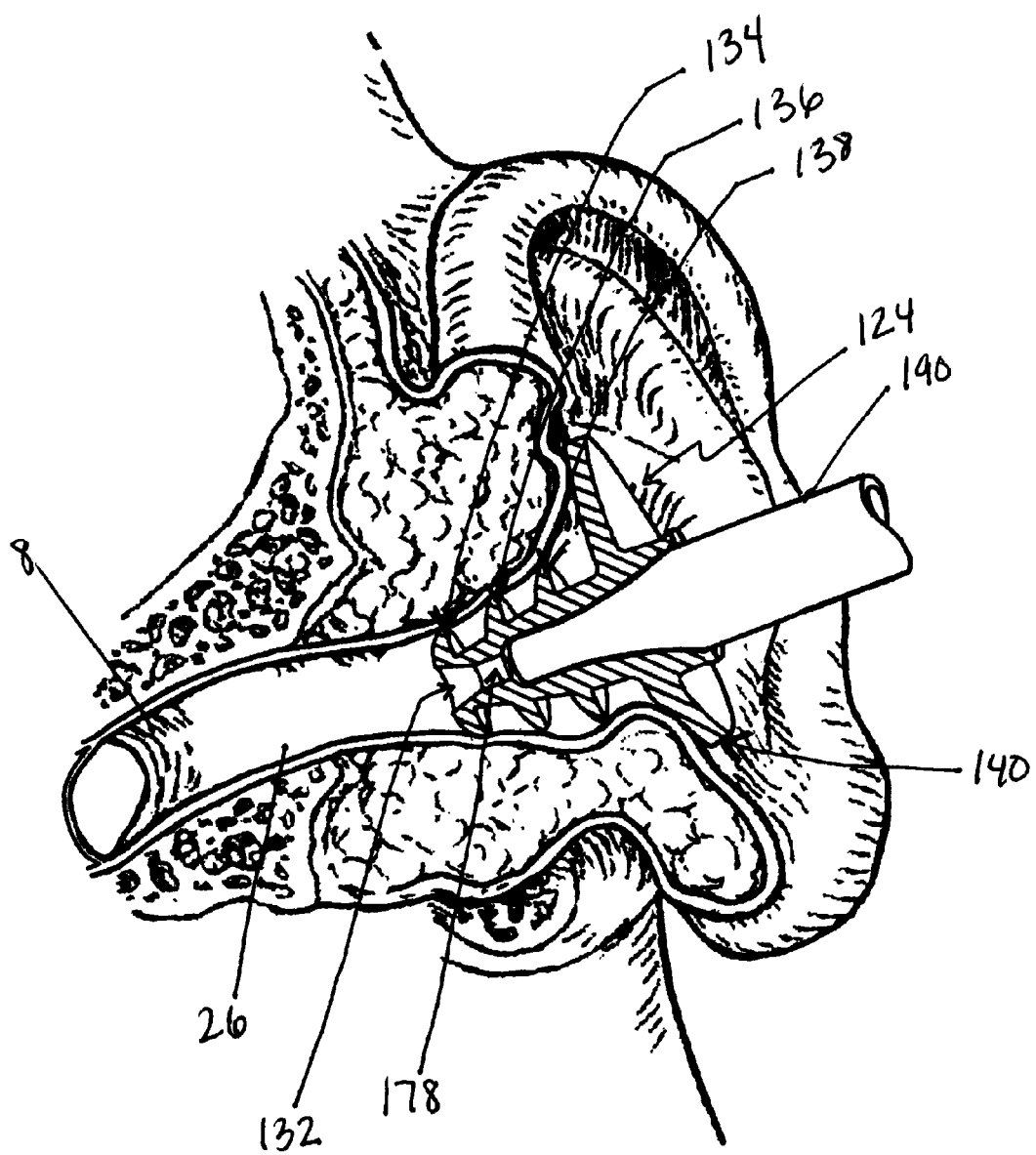
FIG. 26 is a cross-sectional view of the alternate embodiment of FIG. 21 positioned in a patient's ear with a medication applicator inserted.

Referring to FIG. 26, the treatment delivery device 124 is depicted in the external ear canal 26 of the patient. Also depicted is the eardrum 8 of the patient's ear (not to scale). The minor disks 134, 136, and 138 of treatment delivery device 124 are dimensioned such that they form a resilient seal with the wall of the external ear canal 26. A medication applicator tip 190 is also shown within the treatment delivery device 124. The medication applicator tip 190 is designed such that it is seated within the contours of internal lumen 132 to form a seal. The medication applicator tip 190 is adjacent to molded, resilient valve 180.

Figure 27:
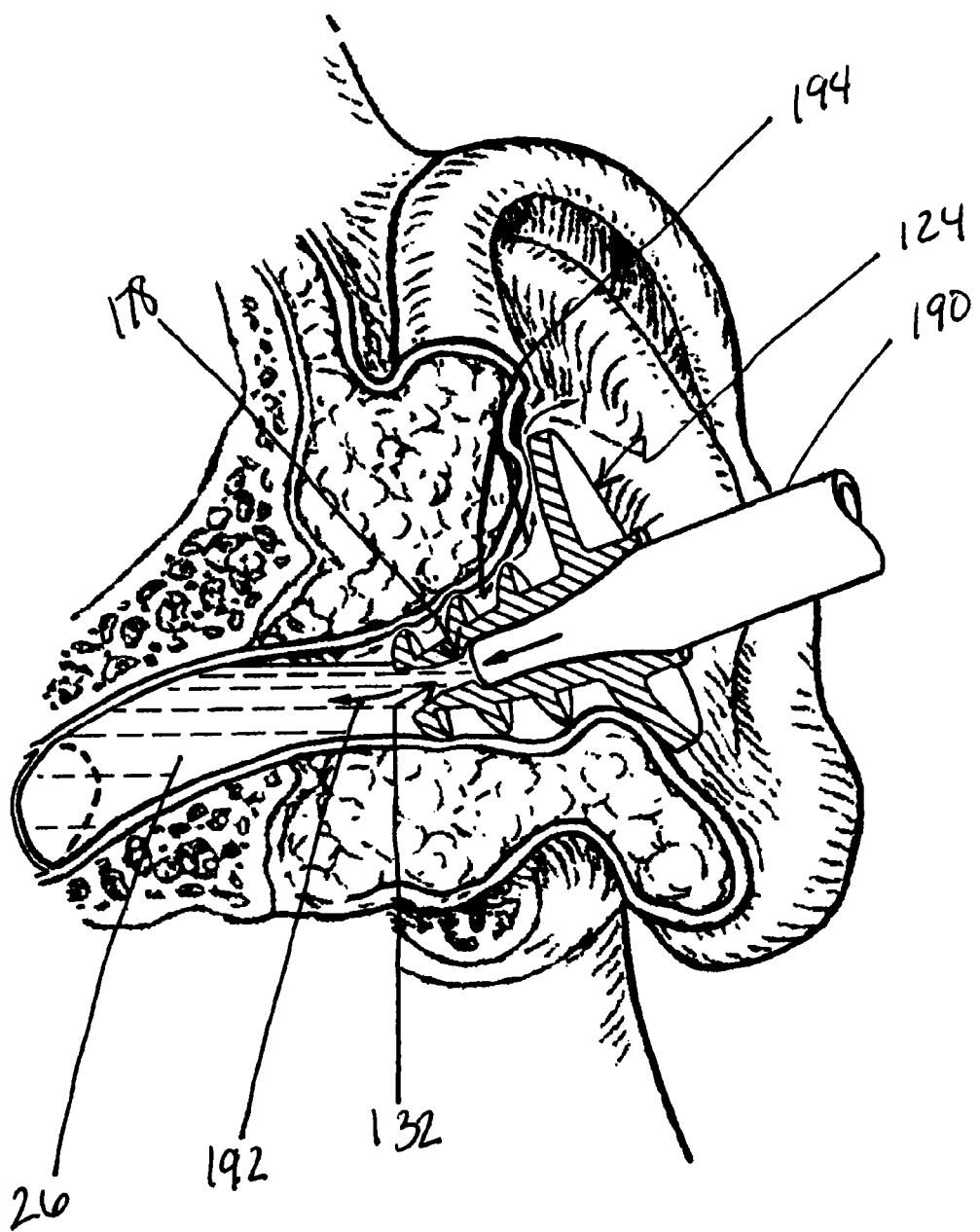
FIG. 27 is a cross-sectional view of the alternate embodiment of FIG. 21 positioned in a patient's ear with treatment fluid being delivered via an inserted medication applicator.

Referring to FIG. 27, the treatment delivery device 124 is shown in the external ear canal 26 of the patient. The minor disks 134, 136, and 138 of treatment delivery device 124 are dimensioned such that they form a seal with the wall of the external ear canal 26. The medication applicator tip 190 is also shown within the treatment delivery device 124. The medication applicator tip 190 is designed such that it is seated within the contours of internal lumen 132 to form a seal. The minor disks 134, 136, and 138 are resilient to a degree such that under air pressure of air displaced by the entrance of fluid through molded, resilient valve 178 minor disks 134, 136, and 138 "give" to permit the escape of displaced air 194 as depicted by small arrows. The medication applicator tip 190 is adjacent to molded, resilient valve 178. The molded, resilient valve 178 opens in either direction under a preselected fluid pressure and closes below the preselected fluid pressure. A treatment fluid 192 is depicted exiting the molded, resilient valve 178 after the preselected fluid pressure has been reached. As the treatment fluid 192 departs the treatment delivery device 124, air 194 escapes between external ear canal 26 and treatment delivery device 124.

In operation, a healthcare provider inserts the treatment delivery device 124 into the external ear canal 26 of a patient, as depicted in FIG. 25. The treatment delivery device 124 is made with a molded, resilient material such as silicone, polyurethane, or some other FDA-approved biocompatible material and gives resiliently to conform to external ear canal 26. The minor disks 134, 136, and 138 of the ear canal engaging portion 126 of the treatment delivery device 124 are dimensioned such that they form a seal with the wall of the external ear canal 26, as depicted in FIG. 26. The major disk 140 of the treatment delivery device 124 sits along the outer edge of external ear canal 26, and affords the healthcare provider access to the internal lumen 132 of the treatment delivery device 124.

In one embodiment of the invention, the healthcare provider inserts the medication applicator tip 190 of a syringe, ear dropper, eye dropper, or similar applicator filled with treatment fluid 192 into the treatment delivery device 124. The healthcare provider then inserts delivery device 124 assembled to medication applicator tip 190 into the external ear canal 26. The medication applicator tip 190 is generally prefilled with treatment fluid 192 prior to assembly with delivery device 124.

The resiliency of the treatment delivery device 124 allows the healthcare provider to stretch the annular medication applicator receiving portion 160 to accommodate medication applicator tip 190, and deliver the treatment fluid 192.

Referring to FIG. 27, the treatment fluid 192 is then delivered into the internal lumen 132 of the treatment delivery device 124. Once the treatment fluid 192 reaches a certain preselected pressure, the valve structure 178 opens and the treatment fluid 192 exits the treatment delivery device 124 and flows into the external ear canal 26 and contacts external ear canal 26 and eardrum 8. Air 194 is displaced when the treatment fluid 192 flows into the external ear canal 26, and escapes between the treatment delivery device 126 and the walls of external ear canal 26. Alternatively, treatment delivery device 124 can be kept in place within the external ear canal 26, with the treatment fluid 192 inside and retained in contact with eardrum 8 and external ear canal 26 structures for a period of time for long-term therapeutic benefit.

It is to be further understood that changes and modifications to the descriptions given herein will occur to those skilled in the art. Therefore, the scope of the invention should be limited only by the scope of the following claims.

What is claimed is:

1. A system of differently sized ear medication delivery devices, comprising:
   a plurality of earplug devices being provided in different outer body sizes for providing a sealing fit with different ear canal sizes, each respective earplug device including:
      a distal end, a proximal end, a fluid lumen extending along a longitudinal axis of the respective earplug device between the proximal end and the distal end, a tube attachment hub along the proximal end and comprising an outer circumferential surface that is positioned radially outward with respect to the longitudinal axis, and a conformable outer annular convex seal surface positioned radially outward from the fluid lumen, wherein at least a portion of the conformable outer annular convex seal surface sealingly engages with an ear canal when the respective earplug device is inserted into the ear canal;
      wherein the fluid lumen extends from the tube attachment hub at the proximal end of the respective earplug device to a distal fluid delivery port axially aligned with the longitudinal axis at the distal end of the respective earplug device;
      wherein the respective earplug device further comprises a fluid drain hole formed in the conformable outer annular convex seal surface at a position that is laterally offset from the longitudinal axis of the respective earplug device, the fluid drain hole having a lateral width that is smaller than a lateral width of the fluid lumen extending along the longitudinal axis of the respective earplug device, wherein the fluid drain hole is configured to drain at least a portion of a treatment fluid in a proximal direction away from an inner ear region after said treatment fluid is dispensed distally of the distal fluid delivery port at the distal end of the respective earplug device; and
   a flexible fluid delivery tube engageable with a selected one of said plurality of earplug devices via coupling with the tube attachment hub of the selected one of said plurality of earplug devices, wherein the flexible fluid delivery tube is configured to provide a fluid delivery path for said treatment fluid between a fluid supply reservoir and the lumen of the selected one of said plurality of earplug devices, the flexible fluid delivery tube having a proximal attachment mechanism for connection with the fluid supply reservoir, and the flexible fluid delivery tube having an overall axial length that is greater than an overall axial length of each respective earplug device of said plurality of earplug devices.

2. The system of claim 1, wherein each respective earplug device further comprises an adjustable seal structure positioned along the fluid lumen, wherein the adjustable seal structure is configured to adjust from a first position to a second position in response to fluid pressure within the fluid lumen.

3. The system of claim 2, wherein the adjustable seal structure positioned along the fluid lumen of each respective earplug device comprises a pressure-relief valve that is configured to relieve fluid pressure of said treatment fluid in the ear canal.

4. The system of claim 2, wherein the adjustable seal structure positioned along the fluid lumen of each respective earplug device is a duck-bill valve.

5. The system of claim 2, wherein the adjustable seal structure positioned along the fluid lumen of each respective earplug device is a one-way valve configured to prevent said treatment fluid from passing from the distal end of the earplug device to the proximal end of the earplug device.

6. The system of claim 1, wherein each respective earplug device is configured to sealingly engage the ear canal so that said treatment fluid delivered via the fluid delivery tube and the lumen of the respective earplug device is retained in contact with the ear canal or an eardrum for a selected period of time to provide a therapeutic benefit.

7. The system of claim 6, wherein each respective earplug device is configured to retain said treatment fluid in contact with the ear canal or the eardrum of a patient for the selected period of time while the patient moves between various positions.

8. The system of claim 6, wherein each respective earplug device is configured to retain said treatment fluid in contact with the ear canal or the eardrum of a patient during delivery of said treatment fluid through the fluid path while the patient remains in one of a standing position, a sitting position, and a prone position.

9. The system of claim 1, wherein the flexible fluid delivery tube is configured to deliver said treatment fluid selected from the group consisting of an antibiotic fluid, an antifungal fluid, a steroid fluid, an analgesic fluid, a cleansing fluid, and an irrigation fluid.

10. The system of claim 1, wherein the conformable outer annular convex seal surface of each respective earplug device comprises a pliable, hypoallergenic material.

11. The system of claim 10, wherein the conformable outer annular convex seal surface of each respective earplug device comprises the pliable, hypoallergenic material selected from the group consisting of elastomeric foam, rubber, silicone, silicone putty, vinyl, and acrylic.

12. The system of claim 11, wherein the flexible fluid delivery tube is formed of a material that is different from said material of the conformable outer annular convex seal surface of each respective earplug device.

13. The system of claim 1, wherein the conformable outer annular convex seal surface of each respective earplug device comprises an outer frustoconical shape.

14. The system of claim 1, wherein the conformable outer annular convex seal surface of each respective earplug device comprises an outer spheroidal shape.

15. The system of claim 1, wherein the flexible fluid delivery tube is configured to provide said fluid delivery path from the fluid supply reservoir that comprises a syringe.

16. The system of claim 15, wherein said proximal attachment mechanism comprises a luer connector to mate with a corresponding connector of the syringe.

17. The system of claim 1, wherein the flexible fluid delivery tube is configured to provide said fluid delivery path from the fluid supply reservoir that is connected to a pump mechanism.

18. The system of claim 1,
wherein the flexible fluid delivery tube is configured to provide said fluid delivery path from the fluid supply reservoir that comprises a delivery bulb.

19. The system of claim 18, wherein each respective earplug device further comprises an adjustable seal structure positioned along the fluid lumen, wherein the tube attachment hub of each respective earplug device extends for an axial length that is smaller than the overall axial length of the respective earplug device, and wherein the tube attachment hub of each respective earplug device comprises a proximal end opening that is axially aligned with the longitudinal axis of the respective earplug device.

20. The system of claim 18, wherein each respective earplug device is configured to sealingly engage the ear canal so that said treatment fluid delivered via the fluid delivery tube and the lumen of the respective earplug device is retained in contact with the ear canal or an eardrum for a selected period of time to provide a therapeutic benefit, wherein each respective earplug device is configured to retain said treatment fluid in contact with the ear canal or the eardrum of a patient for the selected period of time while the patient moves between various positions.

21. The system of claim 1, wherein a fluid drain lumen extends proximally from the fluid drain hole formed in the conformable outer annular convex seal surface of each respective earplug device.

22. The system of claim 21, wherein at least a portion of the fluid drain lumen extends side-by-side to the fluid lumen of the respective earplug device.

23. The system of claim 21, wherein the fluid drain lumen extends proximally from the fluid drain hole to a collection reservoir configured to receive said at least a portion of the treatment fluid drained through the drain hole of the respective earplug device.

24. The system of claim 1, wherein the distal fluid delivery port axially aligned with the longitudinal axis of each respective earplug device comprises a distal-most port of the respective earplug device, and wherein a distal-most end of the fluid drain hole defined in the conformable outer annular convex seal surface of the respective earplug device is positioned proximally rearward of the distal-most port.

25. The system of claim 1, wherein the fluid drain hole of each respective earplug device is formed in the conformable outer annular convex seal surface at a position that is laterally offset from the distal fluid delivery port.

26. The system of claim 1, wherein the fluid drain hole of each respective earplug device faces in a direction away from the proximal end of the respective earplug device such that the fluid drain hole is configured to drain said at least a portion of the treatment fluid in the proximal direction away from the inner ear region.

27. The system of claim 1, wherein the tube attachment hub of each respective earplug device extends for an axial length that is smaller than the overall axial length of the respective earplug device.

28. The system of claim 27, wherein the tube attachment hub of each respective earplug device comprises a proximal end opening that is axially aligned with the longitudinal axis of the respective earplug device.

\* \* \* \* \*